(12) United States Patent
Shi

(10) Patent No.: US 6,673,562 B2
(45) Date of Patent: Jan. 6, 2004

(54) DIFFERENTIAL IMMUNOASSAY

(75) Inventor: Qinwei Shi, Etobicoke (CA)

(73) Assignee: Spectral Diagnostics, Inc., Toronto (CA)

( * ) Notice: Subject to any disclaimer, the term of this patent is extended or adjusted under 35 U.S.C. 154(b) by 0 days.

(21) Appl. No.: 09/938,270

(22) Filed: Aug. 23, 2001

(65) Prior Publication Data

US 2002/0177241 A1 Nov. 28, 2002

Related U.S. Application Data

(60) Provisional application No. 60/292,497, filed on May 21, 2001, and provisional application No. 60/227,536, filed on Aug. 24, 2000.

(51) Int. Cl.⁷ ...................... G01N 33/53; G01N 33/543
(52) U.S. Cl. .......................... 435/7.93; 435/7.1; 435/7.9; 435/810; 435/972; 436/501; 436/518; 436/523; 436/536; 436/538; 436/540; 436/819; 424/138.1; 424/174.1; 424/159.1; 424/277.1; 530/300; 530/350; 530/387.1; 530/388.8; 530/389.7; 530/387.3; 530/391.7
(58) Field of Search .................... 530/300, 350, 530/387.1, 388.8, 389.7, 387.3, 391.7; 435/7.1, 7.9, 7.93, 810, 972; 436/501, 518, 523, 536, 538, 540, 819; 424/138.1, 174.1, 159.1, 277.1

(56) References Cited

U.S. PATENT DOCUMENTS

| | | | |
|---|---|---|---|
| 4,857,453 A | 8/1989 | Ullman et al. | 435/7 |
| 4,900,662 A | 2/1990 | Shah et al. | 435/7 |
| 4,952,517 A | 8/1990 | Bahar | 436/518 |
| 5,242,804 A | 9/1993 | Bahar et al. | 435/7.93 |
| 5,290,678 A | 3/1994 | Jackowski | 435/7.4 |
| 5,604,105 A | 2/1997 | Jackowski | 435/7.4 |
| 5,710,008 A | 1/1998 | Jackowski | 435/7.4 |
| 5,747,274 A | 5/1998 | Jackowski | 435/7.94 |

FOREIGN PATENT DOCUMENTS

| | | | |
|---|---|---|---|
| EP | 384130 | 1/1990 | G01N/33/573 |
| WO | WO 91/01498 | 2/1991 | G01N/33/50 |
| WO | WO 92/21973 | 12/1992 | G01N/33/53 |

OTHER PUBLICATIONS

Katus, H.A. et al. J. Mol. Cell Cardiol. vol. 21: pp. 1349–1353 (1989).
Seguin, J.R. et al. J. Thorac Cardiovasc Surg vol. 98: pp. 397–401 (1989).
Hoberg et al, Eur Heart J. vol. 8: pp. 989–994 (1987).
Wang, Jinxia et al. Clin. Chimica Acta vol. 181: pp. 325–336 (1989).
Cummins et al. Am. Heart J. vol. 113(No. 6): pp. 1333–1344 (1987).
Beuerle, John R. et al. Clin. Chimica Acta vol. 294: pp. 115–128 (2000).

*Primary Examiner*—Long V. Le
*Assistant Examiner*—Lisa V Cook
(74) *Attorney, Agent, or Firm*—Klauber & Jackson

(57) ABSTRACT

The invention provides assay methods and kits that in general measure the level of a first analyte in a sample reduced by the level of a second analyte present in the same sample. In one embodiment, where levels of a first analyte from a first source is desirably determined and first analyte in the sample released from a second source is accompanied by proportional co-release of a second analyte, the assay identifies the level of first analyte released only from the first source. For analytes within bodily fluids, the assay can differentiate between elevated levels of analyte specific to the particular physiological or pathological state and elevated levels not specific to the particular state, providing single tests with diagnostic utility.

7 Claims, 15 Drawing Sheets

Free CAIII vs Signal

Biotin Ab vs Signal

FIG. 12A

```
  1 ATG GAC CCC TCC AAG GAC TCG AAG GCC CAG GTC TCG GCC GCC GAG    45
  1 Met Asp Pro Ser Lys Asp Ser Lys Ala Gln Val Ser Ala Ala Glu    15

46 GCC GGC ATC ACC GGC ACC TGG TAC AAC CAG CTC GGC TCG ACC TTC    90
 16 Ala Gly Ile Thr Gly Thr Trp Tyr Asn Gln Leu Gly Ser Thr Phe    30

91 ATC GTG ACC GCG GGC GCC GAC GGC GCC CTG ACC GGA ACC TAC GAG   135
 31 Ile Val Thr Ala Gly Ala Asp Gly Ala Leu Thr Gly Thr Tyr Glu    45

136 TCG GCC GTC GGC AAC GCC GAG AGC CGC TAC GTC CTG ACC GGT CGT   180
 46 Ser Ala Val Gly Asn Ala Glu Ser Arg Tyr Val Leu Thr Gly Arg    60

181 TAC GAC AGC GCC CCG GCC ACC GAC GGC AGC GGC ACC GCC CTC GGT   225
 61 Tyr Asp Ser Ala Pro Ala Thr Asp Gly Ser Gly Thr Ala Leu Gly    75

226 TGG ACG GTG GCC TGG AAG AAT AAC TAC CGC AAC GCC CAC TCC GCG   270
 76 Trp Thr Val Ala Trp Lys Asn Asn Tyr Arg Asn Ala His Ser Ala    90

271 ACC ACG TGG AGC GGC CAG TAC GTC GGC GGC GCC GAG GCG AGG ATC   315
 91 Thr Thr Trp Ser Gly Gln Tyr Val Gly Gly Ala Glu Ala Arg Ile   105

316 AAC ACC CAG TGG CTG CTG ACC TCC GGC ACC ACC GAG GCC AAC GCC   360
106 Asn Thr Gln Trp Leu Leu Thr Ser Gly Thr Thr Glu Ala Asn Ala   120

361 TGG AAG TCC ACG CTG GTC GGC CAC GAC ACC TTC ACC AAG GTG AAG   405
121 Trp Lys Ser Thr Leu Val Gly His Asp Thr Phe Thr Lys Val Lys   135

406 CCG TCC GCC GCC TCC ATC GAC GCG GCG AAG AAG GCC GGC GTC AAC   450
136 Pro Ser Ala Ala Ser Ile Asp Ala Ala Lys Lys Ala Gly Val Asn   150

451 AAC GGC AAC CCG CTC GAC GCC GTT CAG CAG ACT AGG GCC AAG GAG   495
151 Asn Gly Asn Pro Leu Asp Ala Val Gln Gln Thr Arg Ala Lys Glu   165

496 TGG GGC TAC GCC AGT CAC AAC GGT CCT GAC CAC TGG CAT GAA CTT   540
166 Trp Gly Tyr Ala Ser His Asn Gly Pro Asp His Trp His Glu Leu   180

541 TTC CCA AAT GCC AAG GGG GAA AAC CAG TCG CCC GTT GAG CTG CAT   585
181 Phe Pro Asn Ala Lys Gly Glu Asn Gln Ser Pro Val Glu Leu His   195

586 ACT AAA GAC ATC AGG CAT GAC CCT TCT CTG CAG CCA TGG TCT GTG   630
196 Thr Lys Asp Ile Arg His Asp Pro Ser Leu Gln Pro Trp Ser Val   210

631 TCT TAT GAT GGT GGC TCT GCC AAG ACC ATC CTG AAT AAT GGG AAG   675
211 Ser Tyr Asp Gly Gly Ser Ala Lys Thr Ile Leu Asn Asn Gly Lys   225

676 ACC TGC CGA GTT GTA TTT GAT GAT ACT TAT GAT AGG TCA ATG CTG   720
226 Thr Cys Arg Val Val Phe Asp Asp Thr Tyr Asp Arg Ser Met Leu   240

721 AGA GGG GGT CCT CTC CCT GGA CCC TAC CGA CTT CGC CAG TTT CAT   765
241 Arg Gly Gly Pro Leu Pro Gly Pro Tyr Arg Leu Arg Gln Phe His   255

766 CTT CAC TGG GGC TCT TCG GAT GAT CAT GGC TCT GAG CAC ACC GTG   810
256 Leu His Trp Gly Ser Ser Asp Asp His Gly Ser Glu His Thr Val   270
```

FIG. 12B

```
 811 GAT GGA GTC AAG TAT GCA GCG GAG CTT CAT TTG GTT CAC TGG AAC  855
 271 Asp Gly Val Lys Tyr Ala Ala Glu Leu His Leu Val His Trp Asn  285

856 CCG AAG TAT AAC ACT TTT AAA GAA GCC CTG AAG CAG CGC GAT GGG  900
 286 Pro Lys Tyr Asn Thr Phe Lys Glu Ala Leu Lys Gln Arg Asp Gly  300

901 ATC GCT GTG ATT GGC ATT TTT CTG AAG ATA GGA CAT GAG AAT GGC  945
 301 Ile Ala Val Ile Gly Ile Phe Leu Lys Ile Gly His Glu Asn Gly  315

946 GAG TTC CAG ATT TTC CTT GAT GCA TTG GAC AAG ATT AAG ACA AAG  990
 316 Glu Phe Gln Ile Phe Leu Asp Ala Leu Asp Lys Ile Lys Thr Lys  330

991 GGC AAG GAG GCG CCC TTC ACA AAG TTT GAC CCA TCC TGC CTG TTC 1035
 331 Gly Lys Glu Ala Pro Phe Thr Lys Phe Asp Pro Ser Cys Leu Phe  345

1036 CCG GCA TGC CGG GAC TAC TGG ACC TAC CAG GGC TCA TTC ACC ACG 1080
 346 Pro Ala Cys Arg Asp Tyr Trp Thr Tyr Gln Gly Ser Phe Thr Thr  360

1081 CCG CCC TGC GAG GAA TGC ATT GTG TGG CTG CTG CTG AAG GAG CCC 1125
 361 Pro Pro Cys Glu Glu Cys Ile Val Trp Leu Leu Leu Lys Glu Pro  375

1126 ATG ACC GTG AGC TCT GAC CAG ATG GCC AAG CTG CGG AGC CTC CTC 1170
 376 Met Thr Val Ser Ser Asp Gln Met Ala Lys Leu Arg Ser Leu Leu  390

1171 TCC AGT GCT GAG AAC GAG CCC CCA GTG CCT CTT GTG AGC AAC TGG 1215
 391 Ser Ser Ala Glu Asn Glu Pro Pro Val Pro Leu Val Ser Asn Trp  405

1216 CGA CCT CCA CAG CCT ATC AAT AAC AGG GTG GTG AGA GCT TCC TTC 1260
 406 Arg Pro Pro Gln Pro Ile Asn Asn Arg Val Val Arg Ala Ser Phe  420

1261 AAA TGA                                                     1266
 421 Lys ***                                                      422
```

DIFFERENTIAL IMMUNOASSAY

CROSS-REFERENCE TO RELATED APPLICATIONS

Priority under 35 U.S.C. §119(e) is claimed to Provisional Applications Ser. Nos. 60/227,536, filed Aug. 24, 2000, and 60/292,497, filed May 21, 2001, both of which are incorporated by reference herein in their entireties.

BACKGROUND OF THE INVENTION

Innumerable qualitative and quantitative tests are available for detecting the presence or level of particular substances in a sample. Sources of such samples range from industrial environments such as mines, wastewater processing, food quality, soil testing, among many others. In the medical field, tests for substances in bodily fluids are well known, and are aids to prognostication, diagnosis, and monitoring the progression and treatment of various conditions and diseases. In many cases, multiple tests are performed on a sample and a health care professional then makes a presumptive diagnosis based on the various levels of particular analytes in the sample, among other information gained, for example, from examining a patient.

In certain circumstances, particular in the emergency room and ambulance call, time is of the essence in arriving at a diagnosis and initiating appropriate therapy to intervene in the morbidity and mortality of a rapidly deteriorating condition. One such example is diagnosis of a heart attack in an individual with chest pain or recent onset. Multiple diagnoses may be attributable to chest pain, yet diagnosis based on electrocardiogram or levels of cardiac markers released into the circulation are needed for a confirmatory diagnosis and initiation of a course of therapy, which would be unwise in a patient not having a heart attack. Thus, the need for rapid and accurate, early diagnostic tests is apparent for such emergency conditions.

Although such early tests are available, even such tests are not without flaws. For example, diagnosis of a heat attack within six hours of the onset of chest pain is difficult to perform with a single test. While the cardiac marker troponin I has been recently adopted as a single and highly accurate indicator, it is not detectable until after about six hours, leaving a large window where early initiation of treatment would be highly desirable but dangerous without an accurate diagnosis. Another cardiac marker, myoglobin, is released into the circulation earlier than troponin I, but is not specific for cardiac tissue, as skeletal muscle damage also releases myoglobin into the circulation. Additional tests may be performed together with myoglobin to attempt to identify its origin, in order to improve the accuracy of an early diagnosis.

The foregoing example of heart attack is merely one example of a myriad of diagnoses, which if to be carried out with a high degree of accuracy, need additional, corroborative tests. Although the combination of multiple assays performed simultaneously increases diagnostic precision, it is undesirable in that it also increases the complexity of the testing, the coordination of the timing of the separate test procedures and availability of the information, and the amount of information that must be processed manually or otherwise, often under emergency conditions.

It is towards the simplification of multiple analyte diagnostic tests to provide a single readout reliably indicative of a particular diagnosis that the present invention is directed.

BRIEF DESCRIPTION OF THE INVENTION

In its broadest aspect, the present invention provides an assay useful to determine the relative levels at which different analytes are present in a sample. In the present assay, the extent of the readout is related to the level of the first analyte and that of the second analyte. Thus, in one embodiment, the readout provides either a ratio of the level of the first analyte to the second, or the difference in levels between the first analyte and the second analyte.

The assay of the invention is useful for situations in which a ratio or difference between the levels of the first and second analytes is diagnostically useful, and a single readout that takes the two values into consideration in generating a single differential value can be as informative and directive of further action as would be obtaining the individual values and mentally evaluating or arithmetically calculating the difference or ratio, and then acting upon the result. The method of the invention simplifies decision making by internally integrating the results of at least two individual analyte levels.

By way of non-limiting example, the first analyte and second analytes may be markers useful for determining the health status of an individual, wherein the ratio or difference among the markers is diagnostically informative. In a particular embodiment, elevated levels of the first analyte may be indicative of a life-threatening medical event only if the level of the second analyte is not elevated. In another embodiment, the second analyte also being elevated is indicative of an event. In a third and preferred embodiment, an analyte may originate from different bodily sources and the origin is diagnostically useful; the assay of the invention is useful for identifying the source of elevated levels of the first analyte. In this embodiment, the format of the assays of the invention takes advantage of the co-release of another analyte from the bodily source other than the intended source (referred to herein as a non-target-source marker) whose level is effectively subtracted from that of the total level of desired analyte to provide in a single test, a readout specific to the analyte source.

In one broad aspect, the single assay for a preselected analyte is indicated as the level of the first analyte reduced proportionally by the level of a second analyte present in the sample. A reading is obtained only if the first analyte is present, and the detected level of the first analyte is reduced as the level of the second analyte increases.

In the present assay, the relative presence or level of first and second analytes in a given sample is revealed by utilizing a labeling reagent for one of the two analytes that labels that analyte through a reaction that is inhibited by the other analyte. More particularly, in the present assay, the readout is dependent on binding, to one of the analytes selectively, of a labeling reagent complex the formation of which is inhibited by any second analyte present in the sample. Thus, labeling of the analyte targeted by the labeling reagent proceeds in the absence of the second analyte, and a reading is obtained. No reading is obtained when the first analyte is absent from the sample. When both analytes are present in the sample, the labeling reaction proceeds but in a manner that is competitively inhibited by the second analyte. Thus, the relative levels at which the first and second analytes are present in the sample is reflected by the extent to which the first analyte is labeled, and this is ultimately reflected in the readout obtained following performance of the assay.

Thus, in one of its aspects, the present invention provides a method useful to assay a sample to detect the presence or relative levels therein of first and second analytes, the method comprising the step of bringing the sample into contact with a labeling reagent means adapted to form a labeling complex that binds to and thereby labels the first analyte, wherein formation of the labeling complex is inhibited by second analyte present in the sample.

In a preferred aspect of the invention, the labeling reagent means comprises two components: a labeled binding partner for the second analyte, and a conjugate formed by coupling of a second analyte itself and a binding partner for the first analyte. When second analyte is absent, the first analyte is thus labeled by formation of complexes between the first analyte and the first analyte binding partner, and the second analyte and the labeled second analyte binding partner. When present in the sample, however, the second analyte becomes a competitor for binding to the labeled second analyte binding partner, and thereby inhibits binding of that labeled second analyte binding partner to the conjugate, thus reducing labeling of the first analyte.

In a particular embodiment, a method is provided for identifying in a sample the presence or level of a first analyte above the level of a second analyte comprising the steps of
(a) forming a reaction mixture by contacting the sample with reagent means for labeling the first analyte, the labeling reagent means comprising a mobile, labeled binding partner to the second analyte, and a conjugate between the second analyte and a binding partner to the first analyte;
(b) contacting the reaction mixture with an immobilized binding partner to the first analyte;
wherein the extent of formation of a complex comprising the mobile, labeled binding partner to the second analyte, the conjugate between the second analyte and the binding partner to the first analyte, the first analyte, and the immobilized binding partner to the first analyte, is indicative of the presence or level of the first analyte in the sample reduced by the level of the second analyte in the sample. Desirably, the reaction is staged by first bringing the sample into contact with the mobile, labeled binding partner to the second analyte to allow any second analyte in the specimen to become bound thereto, and then presenting the conjugate before finally contacting the resultant mixture with immobilized binding partner to the first analyte. In this way, the inhibitory effect of sample-borne second analyte is maximized, by allow it to react first with the labeled second analyte binding partner before allowing the conjugate to compete therewith for binding.

By way of non-limiting example, the aforementioned binding partners may be antibodies. The label may be colloidal gold. The sample may be, by way of non-limiting example, a bodily fluid, wastewater, a foodstuff; preferably, it is a bodily fluid such as whole blood, serum, plasma, or urine. By way of example, the first analyte may be a cardiac marker, such as myoglobin, and the second analyte may be a different analyte co-released from a non-cardiac source along with the first analyte, such as carbonic anhydrase III which is released from damaged skeletal muscle along with myoglobin. For determining the level of myoglobin originating from the heart, the mobile, labeled binding partner to the second analyte may be a gold-labeled monoclonal anti-carbonic anhydrase III antibody, the conjugate between the second analyte and a binding partner to the first analyte may be a conjugate between carbonic anhydrase III and an anti-myoglobin monoclonal antibody, and the immobilized binding partner to the first analyte may be an anti-myoglobin monoclonal antibody.

The conjugate between the second analyte and a binding partner to the first analyte may be a covalent conjugate between the members, such as is achievable using a homobifunctional or heterobifunctional cross-linking agent or carbodiimide, or it may comprise a single-chain polypeptide on which reside both the second analyte, or an epitope thereof, and a binding partner, or binding portion thereof, to the first analyte, such that each member retains its desired activities within the conjugate or single-chain polypeptide. For example, the conjugate between an antibody to myoglobin and carbonic anhydrase III may include a single-chain polypeptide comprising carbonic anhydrase III and the immunoglobulin heavy chain, which when assembled into the functioning antibody, provides binding sites for myoglobin and a carbonic anhydrase III portion to which the labeled anti-carbonic anhydrase III antibody may bind. The analyte portion of any of the conjugates herein may be the full-length analyte or a fragment bearing the epitope recognized by the corresponding binding partner. The foregoing example may be used to diagnose a heart attack by indicating an elevated level of myoglobin exists over that which may derived from a non-cardiac source. In this case, the level of cardiac and skeletal (i.e., total) myoglobin detected in the assay is reduced by the amount of carbonic anhydrase III present in the sample, the latter equivalent to the level of skeletal muscle-derived myoglobin.

In a second embodiment, a homogeneous assay similar to that above is provided which employs slightly different reagents, but applies the same principles. In this embodiment, a further binding interface is incorporated into the labeling reaction. Particularly, the conjugate between the first analyte binding partner and the second analyte instead introduces a further biotin/streptavidin interaction, and the conjugate thus is represented by two reagents; one in which biotin is conjugated with either the first analyte antibody or the second analyte, and another in which streptavidin or a biotin-binding component thereof is conjugated with the other of the first analyte antibody or the second analyte. In an embodiment, the conjugate reagents are a first conjugate between first analyte antibody and biotin, and a second conjugate between streptavidin and the second analyte.

Thus, a method is provided for identifying in a sample the presence or level of a first analyte above a second analyte, the method comprising conducting an assay following the steps of
(a) forming a reaction mixture by contacting the sample with
(1) a mobile, labeled binding partner to the second analyte,
(2) a conjugate between the second analyte and streptavidin; and
(3) a biotinylated binding partner to the first analyte; and then
(b) contacting the reaction mixture with an immobilized binding partner to the first analyte;
wherein the extent of formation of a complex comprising the mobile, labeled binding partner to the second analyte, the conjugate between the second analyte and streptavidin, the biotinylated binding partner to the first analyte, the analyte, and the immobilized binding partner to the first analyte, is indicative of the presence or level of the first analyte in the sample reduced by the level of the second analyte in the sample.

Desirably, the assay is performed by staging the addition of reagents in step (a), so that sample is first exposed to the mobile labeled binding partner to the second analyte so that any second analyte in the sample becomes bound thereto, before addition of the competitive-binding conjugate between streptavidin and the second analyte.

By way of non-limiting example, the aforementioned binding partners may be antibodies. The label may be colloidal gold. Streptavidin, or a biotin-binding component thereof, or another biotin-binding partner may be used. The sample may be a biological sample such as a bodily fluid: examples include whole blood, serum, plasma, and urine. By way of example, the first analyte may be a cardiac marker, such as myoglobin, and the second analyte may be a different analyte co-released from a non-cardiac source along with the first analyte, such as carbonic anhydrase III released from damaged skeletal muscle along with myoglobin. For determining the level of myoglobin originating from the heart, the mobile, labeled binding partner to the second analyte may be a gold-labeled monoclonal anti-carbonic anhydrase III antibody, the conjugate between the second analyte and a biotin-binding molecule a conjugate between carbonic anhydrase III and streptavidin, a conjugate between biotin and a binding partner to the first analyte may be a biotinylated anti-myoglobin monoclonal antibody, and the immobilized binding partner to the first analyte may be an anti-myoglobin monoclonal antibody.

The conjugate between the second analyte and a binding partner to biotin may be a covalent conjugate between the members, such as is achievable using a homobifunctional or heterobifunctional cross-linking agent or carbodiimide, or it may comprise a single-chain polypeptide on which reside both the second analyte or an epitope thereof, and streptavidin or the biotin-binding portion thereof, such that each member of the conjugate of single-chain polypeptide independently retains its respective binding activity. For example, the conjugate between streptavidin and carbonic anhydrase III may be a single-chain polypeptide comprising carbonic anhydrase III, or an epitope thereof, and streptavidin or a biotin-binding portion thereof, thus providing binding sites for both a biotinylated antibody and anti-carbonic anhydrase III antibody. As mentioned above, the analyte portion of any of the conjugates herein may be the full-length analyte or a fragment bearing the epitope recognized by the binding partner. The foregoing example may be used to diagnose a heart attack by indicating an elevated level of myoglobin exists over that which may derived from a non-cardiac source, in the same manner as described in the previous embodiment. Variations on these embodiments in the selection of the reagents and operation of the components of the test are fully embraced within the spirit and scope of the present invention.

In a preferred embodiment, the first or preselected analyte is an analyte originating from a target source whose level is desirably measured over the same analyte originating from a source other than the target source. A second analyte is a marker that is released from the non-target (other) source in proportion to the level of first analyte released from the non-target source. The assay of the invention subtracts or proportionally reduces, depending on binding partner affinities, from the total level of first analyte (from the target and non-target source) the level of the second analyte, which effectively subtracts the level of the first analyte derived from the non-target source from the readout value.

By selecting the affinities of the binding partners to the analytes and ratio of the components in the conjugates of the invention, as well as using fragments of the analytes comprising the epitope of the analyte recognized by the binding partners, the relative sensitivity of the assay to the first analyte and especially the reduction in value achieved by the presence of any second analyte in the sample may be adjusted to provide an assay which essentially reads out the ratio between the first analyte and the second analyte. For example, if the second analyte is released from the non-target tissue in very small amounts compared to the amount of the target analyte released from the non-target source, use of a higher affinity antibody in the conjugate of the invention to the second analyte in contrast to a lower affinity antibody to the first analyte will increase the sensitivity of the assay to any second analyte present in the sample. Such variations in the invention are within the realm embraced here, and one of skill in the art by following the teachings herein will readily prepare an assay for other analytes or with other operating characteristics, sensitivities, ranges, or other parameters.

Thus, in one embodiment, a method is provided for identifying in a sample the presence or level of a preselected analyte originating from a target source, wherein any level of the preselected analyte in the sample originating from a source other than the target source is associated with an increased level in the sample of a marker from the source other than the target source, the method comprising conducting an assay following the steps of (a) contacting the sample with a labeling reagent comprising (1) a mobile, labeled binding partner to one of the preselected analyte and the marker, (2) a conjugate between the marker and a binding partner to the preselected analyte; and then (c) contacting the resulting sample with an immobilized binding partner to the other of the marker and the preselected analyte;

wherein the extent of labeling of said immobilized binding partner is indicative of the presence or level of the preselected analyte in the sample reduced by the level of the marker originating from the source other than the target source.

In a preferred embodiment, the immobilized binding partner is a binding partner for the analyte, and the labeled, mobile binding partner is a binding partner for the marker.

By way of non-limiting example, the aforementioned binding partners may be antibodies. The label may be colloidal gold. The sample may be a biological sample such as whole blood, serum, plasma, or urine. By way of example, the preselected analyte may be a cardiac analyte, such as myoglobin, and the corresponding marker may be carbonic anhydrase III. For determining the level of myoglobin originating from the heart, the mobile, labeled binding partner to said marker may be a gold-labeled monoclonal anti-carbonic anhydrase III antibody, the conjugate between the marker and a binding partner to the preselected analyte may be a conjugate between carbonic anhydrase III and an anti-myoglobin monoclonal antibody, and the immobilized binding partner to the preselected analyte may be an anti-myoglobin monoclonal antibody. The conjugate between the marker and a binding partner to the preselected analyte may be a covalent conjugate between the members, such as is achievable using a homobifunctional or heterobifunctional cross-linking agent or carbodiimide, or it may comprise a single-chain polypeptide on which reside both the marker or an epitope thereof and a binding partner or portion thereof, such that each member retains the desired activities in the conjugate or single-chain polypeptide. For example, the conjugate between an antibody to myoglobin and carbonic anhydrase III may include a single-chain polypeptide comprising carbonic anhydrase III and the immunoglobulin heavy chain, which when assembled into the functioning antibody, provides binding sites for myoglobin and a carbonic anhydrase III portion to which the labeled anti-carbonic anhydrase III antibody may bind. The foregoing example may be used to diagnose a heart attack, as described above.

In a second embodiment, an assay similar to that above is provided which employs variations in the components, but provides the same objectives. Thus, a method is provided for identifying in a sample the presence or level of a preselected analyte originating from a target source, wherein any level of said preselected analyte in the sample originating from a source other than the target source is associated with an level in the sample of a marker from the source other than the target source, the method comprising conducting an assay following the sequential steps of (a) first contacting the sample with an analyte labeling reagent comprising
  (1) a mobile, labeled binding partner to one of the preselected analyte or the marker,
  (2) a conjugate between the marker and one of biotin and streptavidin, and
  (3) a binding partner to the preselected analyte conjugated to the other of biotin and streptavidin; and then
(b) contacting the sample with an immobilized binding partner to the other of the preselected analyte and the marker;

wherein the extent of labeling of the immobilized binding partner is indicative of the presence or level of the preselected analyte in the sample reduced by the level of the marker in the sample originating from the source other than the target source.

In a preferred embodiment, the analyte labeling reagent comprises (1) a mobile, labeled binding partner to the marker, (2) a conjugate between the marker and streptavidin, and (3) a biotinylated binding partner to the preselected analyte.

In other preferred embodiments, the immobilized binding partner is a binding partner for the analyte.

By way of non-limiting example, the aforementioned binding partners may be antibodies. The label may be colloidal gold. The sample may be a biological sample such as whole blood, serum, plasma, or urine. By way of example, the preselected analyte may be a cardiac analyte, such as myoglobin, and the corresponding marker may be carbonic anhydrase III. For determining the level of myoglobin originating from the heart, the mobile, labeled binding partner to the marker may be a gold-labeled monoclonal anti-carbonic anhydrase III antibody, the conjugate between the marker and streptavidin may be a conjugate between carbonic anhydrase III and streptavidin, the biotinylated binding partner to the preselected analyte may be biotinylated anti-myoglobin monoclonal antibody, and the immobilized binding partner to the preselected analyte may be an immobilized anti-myoglobin monoclonal antibody.

The aforementioned conjugate between the marker and streptavidin may be a covalent conjugate prepared, for example, by use of a homobifunctional or heterobifunctional cross-linking agent or carbodiimide, or may be a single-chain polypeptide on which reside both the marker or an epitope thereof and streptavidin, each retaining its desired activities and ability to participate in the above-mentioned assay. The foregoing example may be used to diagnose a heart attack.

Of course, in the above methods, wherein two binding partners bind to the preselected analyte, each must be capable of recognizing a different binding site on the preselected analyte such that both binding partners can independently bind and permit the final labeled complex to form if the second analyte (marker) is not present at a level relatively greater than that of the first analyte. Moreover, the sensitivities and selectivities of the foregoing assays may be adjusted, for example, depending on the relative levels of the preselected analyte released from the target source, the level released from the non-target source, and the amount of co-release of the non-target-source marker relative to the release of the preselected analyte from the non-target source. The ratios of the components in the various reagents of the assays may be adjusted, and any reduced binding thereby compensated for in another reagent, as an example of the flexibility of the assay for various analytes.

Preferably, the foregoing binding partners are antibodies, and may be monoclonal or polyclonal antibodies. The preselected analyte is preferably a biomolecule, such as a protein, carbohydrate, nucleic acid, lipid, glycoprotein, glycolipid, by way of example, but it is not so limited. The preselected analyte is capable of being recognized by the binding of two different binding partners, preferably antibodies. The preselected analyte may be present in any sample, including that from a human or animal body, foodstuff or food processing or manufacturing facility, domestic or industrial water supply, etc. Preferably, the sample is a bodily fluid from a human. In a preferred embodiment, the sample is whole blood, the preselected analyte is myoglobin, and the marker is carbonic anhydrase III.

The marker that is also present in the sample is preferably a biomolecule, such as a protein, carbohydrate, nucleic acid, lipid, glycoprotein, glycolipid, by way of example, but it is not so limited. The marker is capable of binding to a binding partner for the marker, preferably an antibody, and the presence of any marker in the sample is capable of competing for binding to the binding partner to the marker with a conjugate comprising the marker, as described above.

The multiple steps in the foregoing examples of the assay of the invention described above may be best illustrated by specific example. Elevated levels of circulating myoglobin, a cardiac and skeletal muscle protein, may be diagnostic for a heart attack if the myoglobin is of cardiac (heart) origin and not from skeletal muscle. Elevated circulating myoglobin from skeletal muscle may indicate muscle damage. While other, more specific cardiac markers are available, myoglobin is particularly desirable if its source can be determined, as it is released early following heart muscle damage, in contrast to other more specific cardiac markers, which are detectable later (for example, after six hours). The method of the present invention provides the level of myoglobin of cardiac origin over that of skeletal origin by taking advantage of the simultaneous release from skeletal muscle of carbonic anhydrase III (CAIII) together with myoglobin. Thus, the first method described hereinabove employs a test strip with 1) a mobile, labeled anti-carbonic anhydrase III antibody; 2) a mobile covalent or single-chain polypeptide-containing conjugate between carbonic anhydrase III and anti-myoglobin antibody; and 3) anti-myoglobin antibody immobilized at the capture zone. In the presence of myoglobin in the sample, myoglobin will form an immunocomplex with the mobile carbonic anhydrase III-anti-myoglobin antibody conjugate, which will be captured at the capture zone by the immobilized anti-myoglobin antibody. The mobile, labeled anti-carbonic anhydrase III antibody will bind to the carbonic anhydrase III on the conjugate, forming a positive band due to the presence of the label. However, in the presence of both myoglobin and carbonic anhydrase III in the sample, the level of binding of the labeled anti-carbonic anhydrase antibody to the mobile carbonic anhydrase III-anti-myoglobin antibody conjugate will be reduced and therefore less will be available to bind to the carbonic anhydrase III on the conjugate, and a reduced or negative result will be obtained, depending on the amount of carbonic anhydrase III present in the sample.

In the second method described above which employs slightly different reagents, myoglobin in the sample will form an immunocomplex with the biotinylated anti-myoglobin antibody, which will then be captured at the capture line by the immobilized anti-myoglobin antibody. The conjugate (covalent or single-chain polypeptide) between streptavidin and carbonic anhydrase III will bind to the biotinylated antibody at the capture line, and the mobile, labeled anti-carbonic anhydrase III will further bind to the streptavidin-carbonic anhydrase III conjugate in the complex, forming a positive band. However, in the presence of both myoglobin and carbonic anhydrase III, the level of binding of the mobile, labeled anti-carbonic anhydrase III antibody to the streptavidin-carbonic anhydrase III conjugate will be reduced by the any carbonic anhydrase III in the sample, and therefore will no longer be available to bind to the immobilized complex. A reduced or negative result will be obtained, depending on the amount of carbonic anhydrase III in the sample.

Depending on antibody affinities, sample flow, volumes, and other parameters, the foregoing assay reduces myoglobin detectability approximately to the extent of the presence of carbonic anhydrase III, in a reciprocal relationship. Modifications of the foregoing methods which achieve the same objectives are likewise embraced herein.

It will further be appreciated that formats alternative to the lateral flow, strip-based format can also be utilized to perform the present assay. In particular, and in embodiments of the invention, the assay is performed in ELISA format, using for instance standard microwell trays convenient for use in robotic readers. In this format, for instance, the sample is mixed with the analyte labeling reagent, and the mixture is then contacted with a binding partner for one of the analytes, desirably the preselected analyte that has been immobilized in the standard way. Following incubation to allow formation of the labeling complex, unbound sample is removed by washing, and a reading is then taken of the immobilized label.

Other pairs of first and second analytes for which knowledge of a ratio or difference in levels is diagnostically useful include fatty acid binding protein and carbonic anhydrase III, and myosin light chain and carbonic anhydrase III for the diagnosis of heart attack; and total cholesterol and high-density lipoprotein (HDL) for assessing risk of atherosclerotic diseases.

The invention is also directed to conjugates or single-chain polypeptides comprising a biotin-binding protein or protein fragment, such as streptavidin, and an analyte, or anti-analyte-binding epitope thereof, to provide a reagents useful in the practice of the invention. For example, a single-chain polypeptide comprising streptavidin and carbonic anhydrase III is useful as the reagent which can bind both a biotinylated antibody and an antibody to carbonic anhydrase III, the utility of which in the practice of the invention is evident from the teachings herein. An example is the single-chain polypeptide shown in SEQ ID NO:1, but this is merely illustrative of a wide variety of conjugates of analytes and biotin-binding molecules that are embraced herein, and may be further extended beyond biotin-streptavidin to other high-affinity binding pairs between one molecule and another, each of which may be separately incorporated into reagents and retain their binding activity. The foregoing conjugates preferably may be prepared by recombinant techniques, wherein a single-chain polypeptide comprising the analyte and streptavidin, joined by a linker peptide, are expressed from a single polynucleotide construct. The invention further embraces polynucleotide sequences encoding such conjugates, such as those that encode SEQ ID NO:1. Alternatively, cross-linking agents may be used to form the reagent. Such include homobifunctional, heterobifunctional, carbodiimides, and such conjugation methods involving covalently linking, with or without a spacer, one functional group of a biomolecule to another is well known in the art.

Another reagent embraced by the present invention is a conjugate of single-chain polypeptide comprising a portion of an antibody (or antigen-binding domain thereof) and a biotin-binding protein or fragment thereof, such that the conjugate, single-chain polypeptide or full antibody may independently recognize and bind to both its epitope and to biotin. The use of this reagent in the practice of the present invention will be evident from the teachings herein. By was of non-limiting example, a reagent comprising streptavidin or a biotin-binding portion thereof covalently bound to an anti-carbonic anhydrase antibody, is described. These reagents may be made by, for example, a bifunctional cross-linking reagent to covalently bind the members of the reagent together, or it may be prepared by recombinant methods, for example, in the construction of a polynucleotide that expresses an immunoglobulin heavy chain with a biotin-binding fragment of streptavidin fused, with our without a linker sequence, to the C-terminal portion of the heavy chain. Association of this single-chain hybrid immunoglobulin molecule with the immunoglobulin light chain will provide a modified antibody molecule capable of both recognizing and binding the intended epitope, and also binding to biotin. This is merely illustrative of methods of preparation and is not intended in any way to be limiting.

The invention also embraces polynucleotide sequences encoding such single-chain polypeptide compositions comprising an immunoglobulin light or heavy chain and a biotin-binding protein or peptide such as streptavidin. A non-limiting example is a polynucleotide sequence which encodes SEQ ID NO:1.

Thus, the invention is also directed to a conjugate comprising an analyte or a fragment thereof, and streptavidin or a biotin-binding equivalent thereof e.g., a biotin-binding variant or fragment of streptavidin, wherein independently, the analyte or fragment thereof in the conjugate is capable of being bound by an antibody to the analyte, and said streptavidin or biotin-binding fragment thereof in the conjugate is capable of binding to biotin. In a preferred embodiment, the analyte or fragment thereof is a protein or peptide. In a further embodiment, the protein or peptide analyte or fragment thereof and streptavidin or a biotin-binding fragment thereof reside on a single polypeptide chain. In a non-limiting example, the analyte is carbonic anhydrase III. An example of such a single-chain polypeptide is depicted in SEQ ID NO:1.

In another embodiment, the invention is directed to conjugate comprising (1) an antibody to a first analyte or a binding fragment thereof, and (2) a second analyte (marker) or a fragment or variant thereof which competes with the second analyte for binding to antibody to the second analyte. In conjugated form, the antibody component in the conjugate is capable of binding the first analyte, and the second analyte component is capable of being bound by an antibody to the second analyte. In one embodiment, the second analyte or fragment thereof is a protein or peptide. In a further embodiment, the second analyte or fragment thereof and a heavy chain or light chain of the antibody reside on a single polypeptide chain. In another embodiment, the second analyte is carbonic anhydrase III and the first analyte is myoglobin. In other embodiments, the second analyte is carbonic anhydrase III and the first analyte is fatty acid binding protein, myosin light chain or any other analyte released from cardiac tissue. The invention also embraces polynucleotides encoding a single-chain polypeptide comprising the immunoglobulin light or heavy chain and an analyte or fragment thereof.

The invention is also directed to kits comprising some or all of the various reagents hereinbefore described in order to carry out any of the assays described and variations therefore embraced herein. Referring to the first analyte as analyte and the second analyte as marker, the following kits are embraced herein:

Kit I
  1) a labeled binding partner to the analyte;
  2) a conjugate between the marker and a second binding partner to the analyte; and
  3) an immobilized antibody to the marker.

Kit II
  1) a labeled binding partner to the marker
  2) a conjugate between the marker and a binding partner to the analyte; and
  3) an immobilized second binding partner to the analyte.

Kit III
  1) a labeled binding partner to the analyte;
  2) either
    a) a second binding partner to the analyte conjugated to biotin, and
    b) a conjugate between the marker and a biotin-binding reagent or
    c) a second binding partner to the analyte conjugated to a biotin-binding reagent, and
    d) a conjugate between the marker and biotin; and
  3) an immobilized binding partner to the marker.

Kit IV
  1) a labeled binding partner to the marker
  2) either
    a) a binding partner to the analyte conjugated to biotin and
    b) a conjugate between the marker and a biotin-binding reagent or
    c) a binding partner to the analyte conjugated to a biotin-binding reagent, and
    d) a conjugate between the marker and biotin; and
  3) an immobilized second binding partner to the analyte.

In the foregoing kits, the binding partners are preferably antibodies or binding portions thereof, and both the binding partner to the analyte and the second binding partner to the analyte capable of simultaneously binding to the analyte. The conjugates comprising the marker may comprise an epitope of the marker. The immobilized binding partner may be provided in the form of a capture line on a test strip, or it may be in the form of a microplate well surface or plastic bead, by way of non-limiting examples. The kits may be used in a homogeneous format, wherein all reagents are added to the sample simultaneously and no washing step is required for a readout, or the kits may be used in a multi-step procedure where successive additions or steps are carried out, with the immobilized reagent added last, with an optional washing step. The teachings herein will allow a skilled artisan to prepare other variations in kit componentry and assay format which carry out the assay of the invention and variations fully embraced herein. Other reagents and instructions may be included with the foregoing reagents.

These and other aspects of the present invention will be better appreciated by reference to the following drawings and Detailed Description.

BRIEF DESCRIPTION OF THE FIGURES

FIGS. 12A–B depicts a single-chain polypeptide comprising carbonic anhydrase III and streptavidin (SEQ ID NO:1), joined by a two-amino-acid linker, which binds to biotin and also to an anti-carbonic anhydrase III antibody.

DETAILED DESCRIPTION OF THE INVENTION

Figure 1:
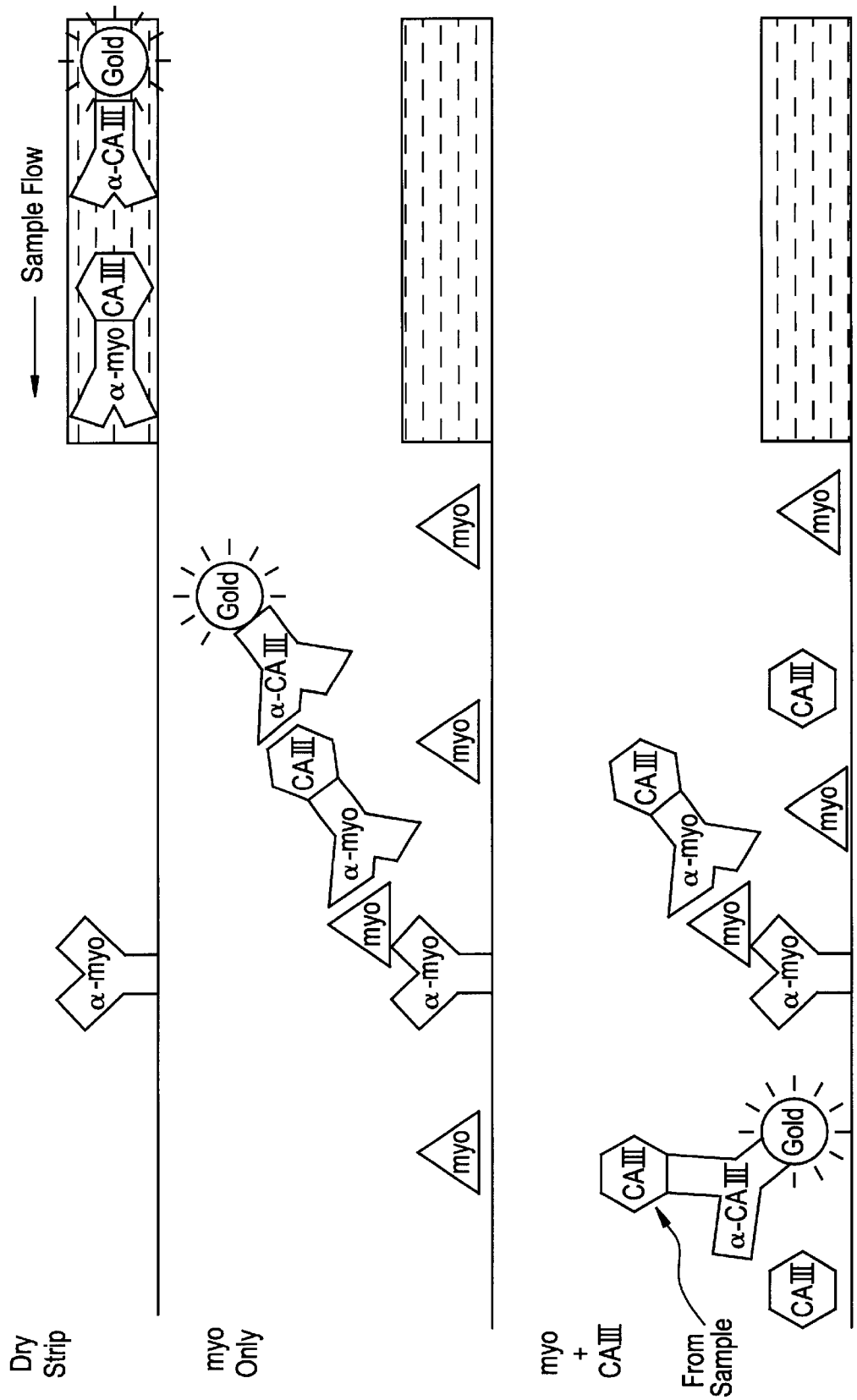
FIG. 1 depicts schematically an assay of the invention, using a lateral flow strip format, for detecting cardiac-specific myoglobin by subtracting, from the detection of myoglobin, any carbonic anhydrase III (CAIII) present in the sample, which is co-released with myoglobin from non-cardiac sources. An immobilized anti-myoglobin antibody is provided at the capture line, and two mobile conjugates, representing the analyte labeling reagent, are utilized: a detectable (gold-labeled) anti-CAIII antibody conjugate, and a CAIII-anti-myoglobin antibody conjugate.

As used herein, "preselected analyte" or "first analyte" refers to a particular substance to be measured in an assay of the invention and expressed as the difference between or ratio over a second analyte. In a particular embodiment, the preselected analyte may be a protein that may be released into a bodily fluid from a particular ("target") bodily source under a certain physiological or pathological condition desirous of being determined, and may also be released from another ("non-target") bodily source, the release therefrom unrelated to the physiological or pathological condition desirous of being determined, and thus responsible for obscuring the usefulness of the preselected analyte as a condition-specific marker.

"Non-target-bodily source" refers to the origin of a preselected analyte not related to the physiological of pathological condition being determined by the methods herein.

"Non-target-bodily-source marker," also referred to simply as "marker" for brevity, refers to an analyte that is co-released with the preselected analyte into the bodily fluid from source(s) other than the target source. It is also referred to as the "second analyte" in the general methods described herein. Thus, in the instance of the present method being used diagnostically for the human body, the level of the non-target-bodily-source marker in the bodily fluid is proportional to the level of preselected analyte not of the origin desirous of being assessed by the methods herein.

"Homogeneous" indicates that the assay, certain embodiments, is performed on the sample in a single step, as far as the user is concerned, without the need, as in heterogeneous assays, for adding reagents, washing or collecting intermediate samples, etc., and that a positive readout, e.g., formation of color at the capture line, is indicative of a positive result, i.e., that the preselected analyte from the target source is present in the sample.

This application claims priority under 35 U.S.C. §119(e) to Provisional Applications serial Nos. 60/227,536, filed Aug. 24, 2000, and 60/292,497, filed May 21, 2001, both of which are incorporated by reference herein in their entireties.

The present assay is suitably applied using an immunoassay format which is capable of detecting the difference or ratio between levels of two or more analytes in a biological sample and providing a single readout indicative of, for example, the level of one analyte minus that of the other. Depending on the relative affinities of the various reagents and binding partners used in the assay, the method can also readout the ratio among the analytes. Such a readout is useful when the level of a second analyte is needed to interpret the diagnostic value of the level of the first analyte. The first analyte must be present to obtain any reading, but its level is reduced by the level of the second analyte, and more particularly by employing a preselected analyte labeling reaction in which a binding partner for the preselected analyte and the second analyte compete for binding to the label.

This format may be used in several ways, one of which is to read out the ratio of differences in levels among two analytes, wherein the ratios are diagnostically useful, such as but not limited to total cholesterol and high-density lipoprotein (HDL) for assessing risk of atherosclerotic diseases. The format may also be used to identify the origin or source of an elevated level of a circulating analyte or marker, if more than one source is possible, provided release of the analyte from a second source is accompanied by release of another marker specific to that second source. This may be performed qualitatively or quantitatively by the methods herein.

By way of example to place this invention in perspective, an example related to the early and accurate diagnosis of a heart attack is illustrated. Cardiac troponin I is a heart-muscle-specific marker which, if detected at elevated levels in circulation, is absolutely diagnostic of a heart attack. However, it is not present in detectable levels until about 6 hours following a heart attack, and such a delay in accurate diagnosis after onset of chest pain may delay the administration of critical therapies, such as fibrinolytic therapy, to reduce the morbidity and mortality of the disease. However, fibrinolytic therapy if administered to an individual not suffering from a heart attack may have serious complications (e.g., hemorrhage). Thus, early and specific diagnosis is highly desirable.

In contrast to the specificity of the foregoing "late" marker troponin I, following a heart attack, the muscle damage marker myoglobin is detectable in circulation much earlier than troponin I, but myoglobin may also released from skeletal muscle following skeletal muscle injury. It thus is an ideal early heart attack marker if its specific release from heart (or lack of specific release from skeletal muscle) can be assessed. However, elevated myoglobin levels could mean heart attack, skeletal muscle injury, or both. As noted above, successful early therapy (and lack of complications) is critically dependent on an accurate diagnosis.

Simply measuring circulating myoglobin does not provide the needed diagnostic accuracy, since its source is not determinable. To determine whether an elevated level of myoglobin is of cardiac or non-cardiac origin, the single-readout assay of the present invention takes advantage of the simultaneous release from injured non-cardiac muscle of both myoglobin and carbonic anhydrase III (CAIII). The latter is not released from heart muscle as a consequence of heart attack. Thus, separate assays for both myoglobin and carbonic anhydrase III could be used diagnostically to identify a heart attack, if the health care professional, when interpreting the results of these two assays, subtracts from the myoglobin value (representing this marker possibly derived from both cardiac and skeletal sources) its equivalent in carbonic anhydrase III level (taking into consideration the relative ratio of myoglobin to carbonic anhydrase III release from injured skeletal muscle). This is a complicated calculation. However, to simplify the calculation and interpretation of these results, an assay of the invention may quantitatively read out only the level of myoglobin of cardiac origin, by essentially subtracting from the total myoglobin levels the equivalent amount of skeletal myoglobin present based on the amount of carbonic anhydrase III in the sample. Or in the instance of a qualitative assay, a positive signal may be generated only if the myoglobin level of cardiac origin is above a preestablished value indicative of a heart attack.

The methods of the invention are applicable to any combination of analytes, preferably pairs but it is not so limiting. Moreover, the relative amounts of the first and second analyte and the differentiating ability of the assay can be adjusted by selection of the appropriate affinities of the binding partners, preferably antibodies, of the various reagents of the assay. Thus, if the second analyte is released at very small amounts relative to the first marker, by use of a higher affinity antibody to the second analyte relative to the affinity of the antibody to the first analyte, in the various reagents of the invention, will have the effect of giving more weight to the level of the second analyte in reducing the readout of the assay. These variations can be readily determined to give a signal based on the relative levels and cutoff values of the analytes.

A physiological or pathologic condition identifiable or diagnosable by detecting the presence in a bodily fluid of elevated levels of a marker or analyte that is specific to the condition is relatively easy to assess, as the mere presence of the analyte or increase over normal levels is indicative of the condition. Such analytes are usually unique to a particular bodily source or are only released from a single bodily source or site of the particular condition. However, many analytes often are not unique or specific to particular condition, and the same analyte is releasable from both the affected bodily source and possibly other sources, confounding any ascribing of the elevated levels to any one source. Thus, the present invention offers a method for providing the necessary specificity to an assay for a particular analyte by taking advantage of the co-release from the non-target bodily source of another analyte, herein referred to as the non-target-bodily-source marker (or simply, "marker"), which when present in circulation indicates that the desired analyte is not wholly or in part from the source of interest. While a separate assay for the non-target-bodily-source marker could be carried out concurrently with the preselected analyte, with the diagnostician ignoring or reducing the presence or extent of the desired analyte based on the detected level of the co-released marker, such interpretation of multiple tests, particularly under emergency conditions, is tedious and subject to error. An assay has been devised herein which reads out analyte level only from the bodily source of interest, reducing or preventing a read-out if the co-released marker is present concurrently. As noted, this is achieved using an analyte labeling reaction that is inhibited by marker present in the sample. Thus, the assay behaves as if the analyte is indeed target-specific for the particular pathology, and eliminates any need for the user to correlate multiple positive and/or negative values with the outcome.

In a further example of the methods herein, a method is provided for determining with an assay the effective filtering capacity of a filter based on changes in pore size. This is applicable in vivo to measuring kidney damage, as it is known that adverse changes in the glomerulus, for example as a consequence of diabetic renal disease, lead to lack of selective filtering (and retention) of large molecules from the blood. With deterioration, larger and larger molecules fail to be retained by the kidneys and appear in the urine. Thus, in the practice of the invention, a first analyte may be a small peptide molecule known to pass easily through the renal filtering system into the urine in the presence or absence of kidney disease. The second analyte may be a larger protein which in normally-functioning kidneys is not excreted in the urine, but with increasing kidney damage, becomes excreted to an ever-increasing extent. In the absence of renal damage, the assay will detect the level of the peptide, indicating normal renal function. With increasing renal damage and excretion of the larger protein, the assay readout declines proportional to the level of the larger protein, indicating a decline in renal function. Thus, a simple renal function test in a test strip format may be prepared following the teachings herein. In a specific embodiment, the analyte pair useful in the assessment of kidney damage is alkaline phosphatase, a normally-secreted small protein, and 5'-nucleotidase, a larger protein the appearance of which indicates tissue damage.

The following table describes some examples of the tests and reagents that may be used to carry out the assays of the invention. These are merely exemplary and non-limiting as to the choices of analytes and markers as well as the format in which the differential assay of the invention is performed.

| Test | | Immobilized | | Labeling Complex | |
|---|---|---|---|---|---|
| Analyte | Marker | reagent | Capture | Conjugate | Labeling Reagent |
| Myo | CA3 | $MyoAb_1$ (1) | $MyoAb_2$:Bn | SAV:CA3 | CA3Ab* (2) |
| Myo | CA3 | $MyoAb_1$ | $MyoAb_2$:CA3 | | CA3Ab* |
| Myo | CA3 | $CA3Ab_1$ | — | CA3:$MyoAb_1$, or CA3:SAV + MyoAb1 :Bn | $MyoAb_2$* |
| Myo | FABP | $MyoAb_1$ | $MyoAb_2$:Bn | SAV:FABP | FABPAb *(3) |
| Myo | MLC | $MyoAb_1$ | $MyoAb_2$:Bn | SAV:MLC | MLCAb* (4) |
| Alk-Phos | 5'-NTase | Alk-PhosAb$_1$ (5) | Alk-PhosAb$_2$:Bn | SAV:'NTase | 5'NTaseAb* (6) |
| LDL | HDL | $LDLAb_1$ | $LDLAb_2$:Bn | SAV:HDL | HDLAb * (7) |
| HDL | LDL | $HDLAb_1$ | $HDLAb_2$:Bn | SAV:LDL | LDLAb* (8) |

Key to abbreviations:
* = detectable label
Myo = myoglobin
Ab = antibody, with subscripts denoting antibodies that recognize different epitopes of the noted antigen to allow concomitant binding of two antibodies to that reagent
:Bn = conjugated biotin
SAV = streptavidin
CA3 = carbonic anhydrase III
CA3: = CA3 conjugated to noted reagent Key to footnotes:
(1) Numerous MyoAbs are available commercially, including for instance from BioDesign International of Saco, Me., USA (2001 Catalog #s H86104M (IgG1), H86142M (IgG1), H86423 (IgG2a), K31013 (IgG2b); and from Spectral Diagnostics Inc. under catalog numbers MA-2010, MA-2040 & PM-1000.
(2) CA3Abs are available commercially, for instance from Spectral Diagnostics under catalog number MA-4010, and from BioDesign.
(3) FABP Abs are available for instance from BioDesign (cat #s H86101M (IgG1), H86294M (IgG2b), and from Spectral Diagnostics under cat #MA-6010.
(4) MLC Abs can be obtained from Spectral Diagnostics under cat #5010 or MLC1-14.
(5) Alk-Phos Abs can be obtained from BioDesign under cat #s K45802M and K45801M.
(6) 5'-NTase Abs can be raised against the enzyme which has the properties reported by Bachmann et al., Kidney International 1997 February; 51(2):479-82 and references therein.
(7) HDL Abs can be obtained from numerous suppliers.
(8) LDL Abs can be obtained from numerous suppliers, including BioDesign (cat #L62308G).

As mentioned above, these assays and commercial sources of reagents for their operation are merely illustrative and non-limiting, and other assays and reagents may be prepared in accordance with the teachings herein.

To describe the general invention in another manner, let $A_t$ represent the first analyte in a sample originating from the target source, and $A_n$ be the same analyte originating from the non-target source. Let B represent a second analyte which is released in proportion to $A_n$ only from the non-target source. The desirable measurement is $A_t$ alone, yet because they are the same analyte, they cannot be distinguished as only total A can be measured. However, because the level of $A_n$ is proportional to the level of B in the sample, the value of $A_t$ can be obtained using ($A_t$ plus $A_n$) minus B. The assay measures $A_t$ plus $A_n$ but reduces the value with increasing levels of B in the sample.

The method is applicable to any assay format, and is conveniently applied, in a homogeneous format, to a dry reagent test strip format. Such test strip formats generally comprise a membrane along which sample flows, picking up mobile reagents, possibly but not necessarily in succession, in a detection zone, and reading out test results at a capture zone where one or more mobile reagents and/or analyte are sequestered at a capture line by an antibody or other specific binding molecule for the analyte. Various bodily fluids may be used, such as but not limited to whole blood, plasma, serum, urine, cerebrospinal fluid, biopsy fluid, and tissue homogenates.

The relative ratio of release of both the analyte and the co-released marker from the non-target source may be factored into the sensitivity and detectability of the source-specific analyte by adjusting the compositions of conjugates used in the assay. Following from the same example above, if the co-released marker is present at only a fraction of the preselected analyte released from the non-target bodily source, a decreased ratio of carbonic anhydrase III in the carbonic anhydrase III-containing conjugate of either assay format will increase the sensitivity of the assay to carbonic anhydrase III. The amount or ratios of other components may also be adjusted to adjust the sensitivity of the assay to provide either the qualitative (yes or no) or quantitative (value) readout. Such adjustments are fully embraced herein.

The method of the invention may be carried out for any analyte for which a marker is co-released with the preselected analyte and is used to effectively subtract or negatively influence the level of preselected analyte of non-target bodily source origin from the analyte from the target source, by the methods herein. Other uses include simply expressing ratios or differences in the levels of two analytes. While several analytes and markers are known, the methods herein offer the development of a large number of new and specific diagnostic tests, using either heterogeneous or homogeneous formats, that do not require sophisticated analysis or interaction by user or computer of the results. Methods for simultaneously measuring the level of numerous analytes in a blood sample, e.g., biological "chips" with sites for a plurality of binding sites for biomolecules, such devices requiring computational analysis of the results and integration of data to provide the results. More simply, individual assays for the preselected analyte and the non-target-bodily-source marker may be performed, the results require mental (or mechanical) integration of the results to arrive at the answer. For example, test strip assay for myoglobin and carbonic anhydrase III may be performed. If myoglobin is elevated, and carbonic anhydrase III is elevated, the origin of circulating myoglobin is likely of non-cardiac oxygen. If carbonic anhydrase III is absent, the myoglobin is likely of cardiac origin. However, such tests require additional reagents, additional samples, assays under similar conditions, and above all, an interpretation of the results of multiple tests to arrive at a conclusion. In contrast, the instant methods are homogeneous, single-test assays that directly read out the desired results. Thus, the methods herein embrace a homogeneous source-specific-assay which detects any analyte. In alternative embodiments, heterogeneous assays are provided which serve the same purposes. The examples described in detail herein are merely exemplary.

While a preferred format for the methods herein are membrane-based test strips which may be used, for example, a whole blood obtained by finger puncture in an emergency room or other point-of-care site, the methods are adaptable to any manual, semi-automated or automated measurement method including but not limited to a single-use test strip read by eye or reflectometer, an automated assay analyzer capable of processing numerous samples, a multiple-analyte test strip, etc. Microtiter plate-based or microbead-based assays are also adaptable for the assay herein, where the immobilized reagent is bound to a microtiter plate well or to a plastic bead. Membrane-based test strips which utilize whole blood are known in the art.

Sources of sample for the assay herein is preferably a biological sample such as whole blood, plasma, serum, urine, cerebrospinal fluid, biopsy specimens, etc., but is not limited thereto and may extend to other sources in which the level of a particular analyte and analyte source of interest may me marked by the same analyte from another source, and the level of analyte from the other source may be gauged by another co-released or coordinately present marker in the sample. Such uses may include food processing and analysis, wastewater, environmental analysis, etc., where the origin of a particular analyte is determinable. By way of illustration only, a test to determine the level, if any, in a reservoir of a particular enteropathogenic coliform bacterial contaminant originating from runoff from a dairy farm may be determined even though the same coliform may originate from the occasional squirrel excrement falling in the reservoir. A test as described herein which detects the coliform but "subtracts" therefrom a squirrel intestine-specific bacterium yields the level of the cattle-derived contaminant.

Thus, an assay format is preferred, in which binding partners such as antibodies can be obtained or prepared for the analytes. As noted, biotin-avidin, biotin-streptavidin or other biotin-binding-reagent reactions can be used to enhance or modulate the test. However, any such assay can be devised using other binding partners to the analyte and marker, including but not limited to extracellular or intracellular receptor proteins which recognize the analytes, binding fragments thereof, hybridization probes for nucleic acids, lectins for carbohydrates, etc. The particular selection of binding partners is not limiting, provided that the binding partners permit the test to operate as described herein. As noted above, the preselected analyte, when present, is detectable by binding by two binding partners, one immobilized on the test strip (or whatever format the assay is provided) and another part of a conjugate. This is taken into consideration in the selection of the reagents for the assay.

The dry test strip may be set up in any format in which contact of the sample with the reagents is permitted and the formation and mobility of the immunocomplexes and other complexes forming therein are permitted to flow and contact an immobilized reagent at the capture line. Various format are available to achieve this purpose, which may be selected by the skilled artisan.

The label portion of the mobile, labeled antibody to the non-target-bodily-source marker may be a visible label, such as gold or latex, an ultraviolet absorptive marker, fluorescent marker, radionuclide or radioisotope-containing marker, an enzymatic marker, or any other detectable label. A visibly detectable marker or one that can be easily read in a reflectometer is preferred, for use by eye, reading or confirmation with a reflectometer. Other labels may be applicable to other semi-automated or automated instrumentation.

The conjugates of the invention may be prepared by conventional methods, such as by activation of an active moiety, use of homobifunctional or heterobifunctional cross-linking reagents, carbodiimides, and others known in the art. Preparation of, for example, a gold-labeled antibody, a conjugate between an antibody and an analyte (not an immunocomplex but a covalent attachment which allows each member to independently exhibit its binding properties), biotinylation of an antibody, conjugation of streptavidin with a protein, immobilization of antibodies on membrane surfaces, etc., are all methods known to one of skill in the art. The preparation of the reagents of the methods herein extend to, for example, recombinant expression of a single-chain polypeptide comprising streptavidin or the biotin binding site of streptavidin or another biotin-binding molecule and at least the epitope of the non-target-bodily-source marker recognized by the antibody to the latter. Thus, a polynucleotide which comprises the coding sequence for each portion, optionally linked by a segment encoding a polypeptide spacer or linker portion, is expressed such that both members on the single-chain polypeptide retain their desired activities in the assay. The invention extends to such single-chain polypeptide reagents useful for the assays described herein, as well as polynucleotides encoding the single-chain polypeptides, as well as expression vectors, microorganisms containing such vectors and related means for expressing such polynucleotides to provide the desired single-chain polypeptides. In another example, recombinant preparation of immunoglobulin molecules in which the polypeptide marker is present in a single-chain polypeptide with either the heavy chain or light chain of the immunoglobulin are embraced herein, such that the assembled immunoglobulin molecule (or fragment) comprises the antigen binding site(s) as well as epitopes of the marker necessary for the operation of the hereinde-scribed assay. Polynucleotides expressing such polypeptides, microorganisms and eukaryotic cells expressing and producing such products including antibodies which comprise a single-chain component with the marker, and other means for preparing such reagents are embraced herein. In a preferred embodiment, the marker polypeptide is fused at the C-terminus of the heavy chain of the particular immunoglobulin class and subclass desired. Moreover, other binding partners for the preselected analyte other than an antibody, such as a receptor, may be provided in a conjugate with the marker in a single-chain or comprising a single-chain polypeptide with the desired activity of both components. Such methods to facilitate the preparation or parameters of the reagents herein, as well as considerations such as ratios between the components, binding affinities, color density, etc., are embraced herein.

One example of such a single-chain polypeptide is described as SEQ ID NO:1, an expression product of a polynucleotide (SEQ ID NO:2) comprising streptavidin and carbonic anhydrase III. The present invention is also directed to this and related compositions. It also extends to polynucleotides encoding the single-chain polypeptides of the invention, such as all of those which encode SEQ ID NO:1. The polynucleotide sequences embraced herein include degenerate variants which encode the same polypeptide sequences, by virtue of the degeneracy of the genetic code, as well as variants in the polynucleotide sequences which result in altered amino acid sequences but are not of consequence in the properties of the expressed hybrid polypeptide.

As noted in the Summary above, the assays of the invention may be provided in two orientations: in one, the labeled reagent is a binding partner to the analyte and the immobilized reagent is a binding partner to the marker; in an alternate embodiment, the labeled reagent is a binding partner to the marker and the immobilized reagent is a binding partner to the analyte. In both assays, a conjugate between the marker and a binding partner to the analyte is used; in the alternate format of either assay with slightly different reagents, in place of the conjugate between the marker and a binding partner to the analyte, the reagent pairs used may be either 1) a binding partner to the analyte conjugated to biotin, and a conjugate of the marker and a biotin-binding reagent such as streptavidin, or 2) a binding partner to the analyte conjugated to a biotin-binding molecule such as streptavidin, and a conjugate of the marker and biotin. Both orientations and reagent selections are fully embraced herein and may be selected depending on the desired sensitivity of the assay, the characteristics of the reagents, the relative ratios of analyte to marker encountered, and other parameters.

The invention is also directed to kits comprising some or all of the various reagents hereinbefore described in order to carry out any of the assays described and variations thereof embraced herein. A kit may have at least one reagent for carrying out an assay of the invention, such as a kit comprising a conjugate between a biotin-binding reagent and a marker, such as a single-chain polypeptide comprising streptavidin and a polypeptide marker. Preferably, the kit comprises all of the reagents needed to carry out any one of the aforementioned assays, whether it be homogeneous, heterogeneous, comprise a single conjugate of the marker conjugated to an antibody to the analyte, or comprise two reagents which serve this function (such as a biotinylated antibody to the analyte plus a streptavidin-marker conjugate, or a biotinylated marker plus a streptavidin conjugated to an antibody to the analyte conjugate), or whether the assay employs an immobilized antibody to the analyte and a labeled antibody to the marker, or an immobilized antibody to the marker and a labeled antibody to the analyte. Referring to the first analyte as analyte and the second analyte as marker, and a second binding partner as a binding partner which recognizes a different epitope than the first binding partner mentioned, the following kits are non-limiting examples of those embraced herein:

Kit I
 1) a labeled binding partner to the analyte;
 2) a conjugate between the marker and a second binding partner to the analyte; and
 3) an immobilized antibody to the marker.

Kit II
 1) a labeled binding partner to the marker;
 2) a conjugate between the marker and a binding partner to the analyte; and
 3) an immobilized second binding partner to the analyte.

Kit III
 1) a labeled binding partner to the analyte;
 2) a second binding partner to the analyte conjugated to biotin;

3) a conjugate between the marker and a biotin-binding reagent; and 4) an immobilized binding partner to the marker.

Kit IV 1) a labeled binding partner to the analyte;

2) a second binding partner to the analyte conjugated to a biotin-binding reagent;

3) a conjugate between the marker and biotin; and 4) an immobilized binding partner to the marker.

Kit V 1) a labeled binding partner to the marker;

2) a binding partner to the analyte conjugated to biotin;

3) a conjugate between the marker and a biotin-binding reagent; and 4) an immobilized second binding partner to the analyte.

Kit VI 1) a labeled binding partner to the marker;

2) a binding partner to the analyte conjugated to a biotin-binding reagent;

3) a conjugate between the marker and biotin; and 4) an immobilized second binding partner to the analyte.

Kit VII 1) a conjugate between the marker and a binding partner to the analyte.

Kit VIII 1) a second binding partner to the analyte conjugated to biotin, and 2) a conjugate between the marker and a biotin-binding reagent.

Kit IX 1) a binding partner to the analyte conjugated to a biotin-binding reagent, and 2) a conjugate between the marker and biotin.

In any of the foregoing kits, the binding partners are preferably antibodies or binding portions thereof, and both the binding partner to the analyte and the second binding partner to the analyte capable of simultaneously binding to the analyte. The conjugates comprising the marker may comprise an epitope of the marker, such that it is recognized by a binding partner to the marker. The conjugates of the kits, if both members are independently peptides or polypeptides, may be in the form of a single-chain polypeptide comprising both members, each exhibiting its activity independently in the single-chain polypeptide. The immobilized binding partner may be provided in the form of a capture line on a test strip, or it may be in the form of a microplate well surface or plastic bead, by way of non-limiting examples of immobilized carriers for binding partners. As mentioned above, the kits with or without immobilized reagent may be used in a homogeneous format, wherein all reagents are added to the sample simultaneously and no washing step is required for a readout, or the kits may be used in a multi-step procedure where successive additions or steps are carried out, with an optional washing step or transfer of components from one container to another. The teachings herein will allow a skilled artisan to prepare other variations in kit componentry and assay format which carry out the assay of the invention and its variations fully embraced herein. Other reagents, containers, and instructions may be included with any of the foregoing kits.

By way of non-limiting example, and following the above example of an assay for detecting myoglobin released from cardiac tissue and reducing it by the level of CAIII that would be co-released with myoglobin from skeletal muscle, the foregoing examples of kits comprise the following reagents in a preferred embodiment:

Kit I 1) a labeled antibody to myoglobin;

2) a conjugate between CAIII and a second antibody to myoglobin; and 3) an immobilized antibody to CAIII.

Kit II 1) a labeled antibody to CAIII;

2) a conjugate between CAIII and an antibody to myoglobin; and 3) an immobilized second antibody to myoglobin.

Kit III 1) a labeled antibody to myoglobin;

2) a second antibody to myoglobin conjugated to biotin;

3) a conjugate between CAIII and streptavidin; and 4) an immobilized antibody to CAIII.

Kit IV 1) a labeled antibody to myoglobin;

2) a second antibody to myoglobin conjugated to streptavidin;

3) a conjugate between the CAIII and biotin; and 4) an immobilized antibody to CAIII.

Kit V 1) a labeled antibody to CAIII;

2) an antibody to myoglobin conjugated to biotin;

3) a conjugate between CAIII and streptavidin; and 4) an immobilized second antibody to myoglobin.

Kit VI 1) a labeled antibody to CAIII;

2) an antibody to myoglobin conjugated to streptavidin;

3) a conjugate between CAIII and biotin; and 4) an immobilized second antibody to myoglobin.

Kit VII 1) a conjugate between CAIII and an antibody to myoglobin.

Kit VIII 1) a second antibody to myoglobin conjugated to biotin, and 2) a conjugate between CAIII and streptavidin.

Kit IX 1) an antibody to myoglobin conjugated to streptavidin, and 2) a conjugate between CAIII and biotin.

Of course, the conjugate between CAIII and streptavidin may be a single-chain polynucleotide comprising CAIII or an anti-CAIII-antibody-binding fragment thereof, and streptavidin or a biotin-binding fragment thereof. The conjugate between CAIII and an antibody to myoglobin may comprise a single-chain polypeptide of CAIII or an epitope thereof and a light or heavy immunoglobulin chain, which is then assembled to provide a hybrid molecule of an anti-myoglobin antibody and CAIII.

Moreover, a kit of the invention may comprise a polynucleotide encoding a single-chain polypeptide comprising CAIII and streptavidin.

The foregoing examples of kits for detecting cardiac myoglobin in a bodily fluid are merely exemplary of this embodiment, and as mentioned above, the reagents may be tailored to measure a large number of other analytes and markers for various purposes.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE 1

Two-conjugate, Qualitative Homogeneous Assay for Heart Attack

FIG. 1 illustrates the design and operation of a membrane strip-format assay which is positive for myoglobin only if carbonic anhydrase III is absent. Present in the detection zone of the test strip is analyte labeling reagent in the form of two mobile reagents: 1) a gold-labeled, affinity-purified polyclonal IgG antibody to carbonic anhydrase III, and 2) a conjugate between CAIII and an anti-myoglobin monoclonal IgG antibody, prepared using a heterobifunctional cross-linking reagent. Immobilized at the capture line is another anti-myoglobin monoclonal IgG antibody, recognizing a different epitope on myoglobin than that of the aforementioned conjugate. The assay format may be as described in co-pending application Ser. No. 09/130,164, filed Aug. 6, 1998, now U.S. Pat. No. 6,171,870, in which a whole blood sample is applied to the device and red blood cells in the whole blood sample are detained in migration providing a red-cell-free plasma front at the capture line for visualization. A 25 microliter sample of whole blood from a patient in the emergency room presenting with chest pain of a few hours' onset, and having a history of poor dietary habits and sedentary life style, is applied to the device, and the results are read after the test complete window indicates the test is complete. During the flow of sample, any myoglobin in the sample forms an immunocomplex with the mobile conjugate comprising the anti-myoglobin antibody and carbonic anhydrase III, and the myoglobin immunocomplexed therewith binds to the immobilized anti-myoglobin antibody. The gold-labeled anti-carbonic anhydrase III reagent binds to the carbonic anhydrase III in the first immunocomplex, forming a colored band at the capture line and indicating the presence of myoglobin in the absence of carbonic anhydrase III. This result is diagnostic of a heart attack. Treatment with fibrinolytic therapy is indicated.

In another example, a sample is obtained by emergency medical technicians at the site of a traffic accident in which an individual with a similar life style as above but with chest pain of onset immediately following the chest striking the automobile steering wheel. The test as above is used. In this case, no colored band forms at the capture line, indicating that if myoglobin was released as a consequence of skeletal trauma in the accident, its level is compensated (i.e., reduced) by the simultaneous release of carbonic anhydrase III. The reaction chain comprising the carbonic anhydrase III-anti-myoglobin antibody, myoglobin, and the immobilized anti-myoglobin antibody forms are a consequence of skeletal muscle myoglobin present in the sample, but the coincident presence of carbonic anhydrase III binds to the labeled anti-carbonic anhydrase III antibody and thus this labeled reagent is not available to bind to the carbonic anhydrase III-anti-myoglobin antibody conjugate at the capture line. A heart attack is ruled out. The patient is treated for chest trauma.

EXAMPLE 2

Three-conjugate, Qualitative and Quantitative Assays for Heart Attack

Figure 2A:
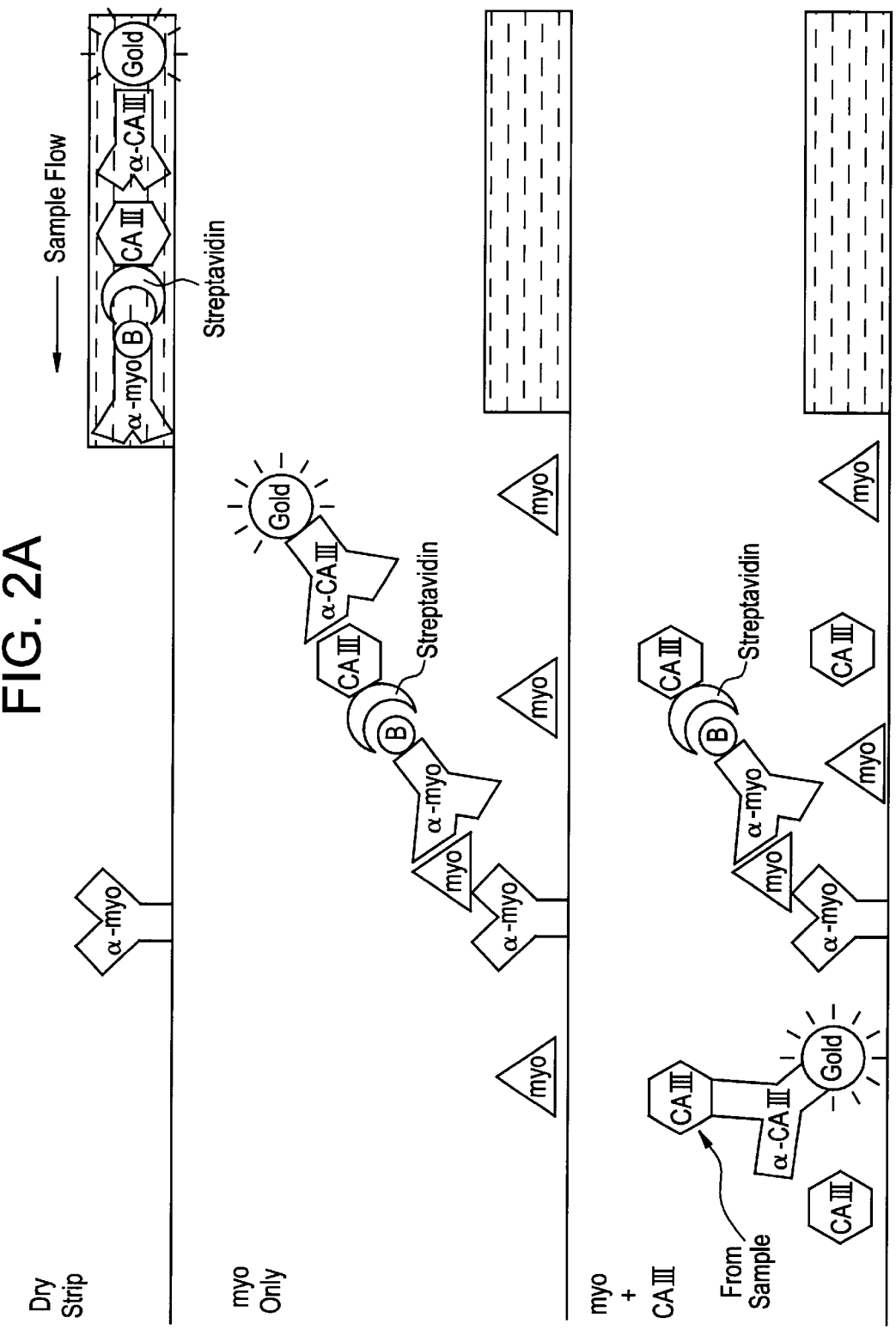
FIG. 2A depicts schematically another embodiment as in FIG. 1, which employs an immobilized anti-myoglobin antibody at the capture line and, representing the analyte labeling reagent, three mobile conjugate reagents: a detectable (gold-labeled) anti-CAIII antibody conjugate, a CAIII-streptavidin conjugate, and a biotinylated anti-myoglobin antibody.

FIG. 2A illustrates the design and operation of a membrane strip-format assay which is positive for myoglobin only if carbonic anhydrase III is absent. Present in the detection zone of the test strip is an analyte labeling reagent in the form of three mobile reagents: 1) a gold-labeled, affinity-purified polyclonal IgG antibody to carbonic anhydrase III, prepared as described in Example 1 above, 2) a conjugate between carbonic anhydrase III and streptavidin, prepared either by engineering a single-chain polypeptide comprising carbonic anhydrase III and streptavidin, or using a heterobifunctional cross-linking agent to cross-link the members, and 3) a biotinylated anti-myoglobin monoclonal IgG antibody. Immobilized at the capture line is another anti-myoglobin monoclonal IgG antibody, recognizing a different epitope on myoglobin than that in the biotinylated reagent. The assay format may be as described in U.S. Pat. No. 6,171,870, incorporated herein by reference in its entirety, in which a whole blood sample is applied to the device and red blood cells in the whole blood sample are detained in migration providing a red-cell-free plasma front at the capture line for visualization. A 25 microliter sample of whole blood from a patient in the emergency room presenting with chest pain of a few hours onset, and a history of poor dietary habits and sedentary life style, is applied to the device, and the results are read after the test complete window indicates the test is completed. During the flow of sample, any myoglobin in the sample forms an immunocomplex with the mobile, biotinylated anti-myoglobin antibody and the immunocomplex binds to the immobilized anti-myoglobin antibody at the capture line. The gold-labeled anti-carbonic anhydrase III reagent binds to the streptavidin-carbonic anhydrase III conjugate, and the streptavidin binds to the now-immobilized biotinylated anti-myoglobin antibody, producing a colored band at the capture line. This result is diagnostic of a heart attack. The patient is treated immediately with fibrinolytic therapy.

Figure 2B:
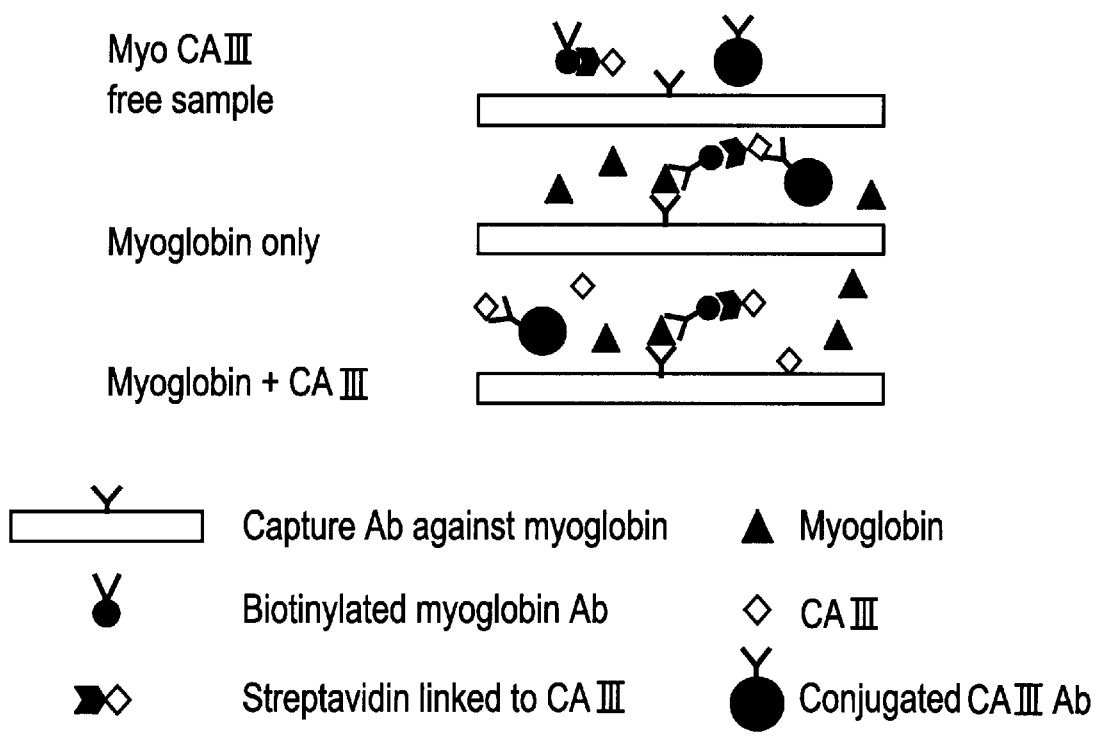
FIG. 2B depicts schematically another embodiment as in FIG. 2A, but using a heterogeneous format.

Similarly, and as shown in FIG. 2B, the same assay depicted in FIG. 2A and described above can be performed using a heterogeneous format, requiring a wash step between incubation of sample with reagents, and detection of label, in order to remove unbound label from the reaction mix. This quantitative assay is carried out according to the following procedure.

1. Coating: Coat wells with 100 microliters of rabbit anti-myoglobin (Spectral Diagnostics Inc.) at a concentration of 5 micrograms per milliliter in 50 mM carbonate/bicarbonate Coating Buffer, pH 9.6 (always prepare in glass). Seal the plate with plate sealer and store at 4 C overnight.
2. Washing: Wash plates 3 times with PBS-0.05% Tween 20 and 1 time with ultrafiltered (UF) water.
3. Blocking: Block the wells with 200 microliters of 1% digested casein at room temperature for 1 hour while shaking at 400 rpm.
4. Repeat washing step 2.
5. Add 50 microliters of sample per well.
6. Add 25 microliters/well of diluent buffer (PBS containing 0.005% Tween 20 and 0.25% BSA) containing 4 micrograms per milliliter of anti-CAIII mAb 2CA-4 (Spectral Diagnostics Inc.) conjugated with HRP.
7. Incubate for 10 min at room temperature with shaking.
8. Add 25 microliters/well of diluent buffer containing 8 micrograms per milliliter of biotinylated anti-myoglobin mAb 2 mb-295 (Spectral Diagnostics Inc.) and 2 micrograms per milliliter of streptavidin-CAIII recombinant protein (Spectral Diagnostics Inc.).
9. Incubate for 30 min at room temperature with shaking.
10. Repeat washing step 2.
11. Add 100 microliters/well of substrate solution (1 OPD tablet, 12.5 ml of phosphate/citrate buffer, pH 5.0, 125 microliters of 3% $H_2O_2$).

12. Incubate for 30 min at room temperature in the dark.
13. Stop reaction with 50 microliters/well of 4 N $H_2SO_4$ and read at 490 nm in a plate reader.

The results from the plate reader are then compared with a standard curve to calculate cardiac myoglobin concentration. A standard curve is generated with the same method using a set of calibrators.

The foregoing details of the procedure are merely exemplary and many variations in its details, such as the conditions for coating, reaction, various concentrations of reagents, buffers, etc., may be varied and remain with the scope of the present invention.

In another example, a sample is obtained by emergency medical technicians at the site of a traffic accident in which an individual with a similar life style as above but with chest pain of onset immediately following the chest striking the automobile steering wheel. The test as above is used. In this case, no colored band forms at the capture line, indicating that if myoglobin was released as a consequence of skeletal trauma in the accident, its level is compensated (i.e., reduced) by the simultaneous release of carbonic anhydrase III. In this case, in the presence of both myoglobin and carbonic anhydrase III, the myoglobin in the sample permits the binding of the carbonic anhydrase III-streptavidin conjugate to the biotinylated anti-myoglobin antibody and the latter to myoglobin on the immobilized anti-myoglobin antibody, but the carbonic anhydrase III present in the sample binds to the gold-labeled anti-carbonic anhydrase III antibody, making it no longer available to bind to the carbonic anhydrase III-streptavidin conjugate, and no color is deposited at the capture line. A heart attack is ruled out. The patient is treated for trauma to the chest, and not with potentially dangerous fibrinolytic therapy.

EXAMPLE 3

Measurement of Myoglobin of Cardiac Origin

Before preparing the reagents and assay format for a homogeneous test to measure the level of myoglobin of cardiac origin, the parameters under which the assay should operate were developed using mathematical models. In this assay, the level of total myoglobin in a sample of blood is subtracted by the level of myoglobin of skeletal origin, the latter determined based on the detection of carbonic anhydrase III, which is co-released with myoglobin from skeletal muscle tissue, but is not released from cardiac tissue. The test parameters are established such that a positive test indicates a sufficiently high amount of myoglobin of cardiac origin is present to diagnose a heart attack. The assay system employed is that described in Example 2, above.

Figure 3:
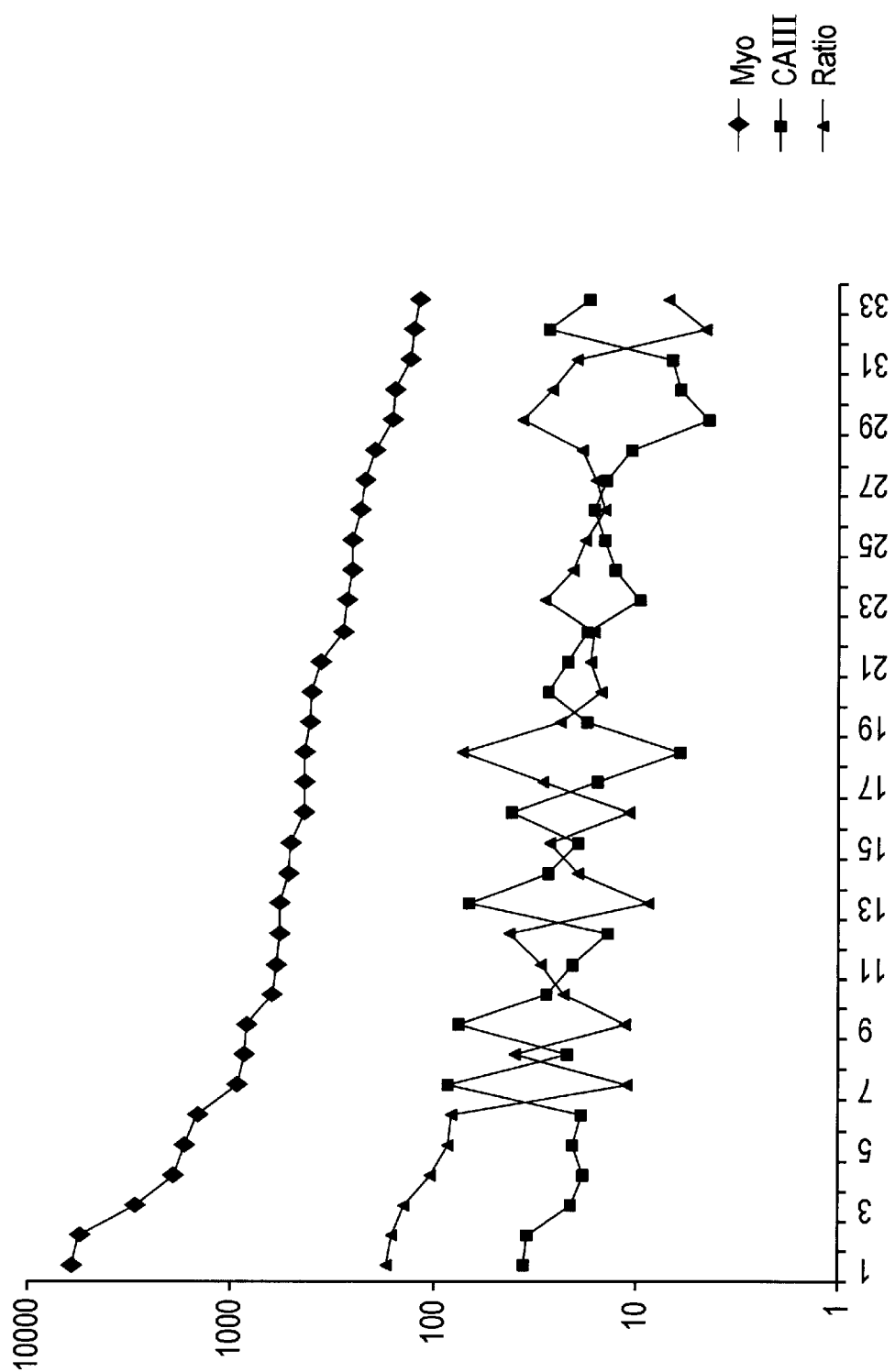
FIG. 3 depicts graphically the myoglobin, carbonic anhydrase III, and the ratio therebetween, in a series of myocardial infarction patients.
Figure 4:
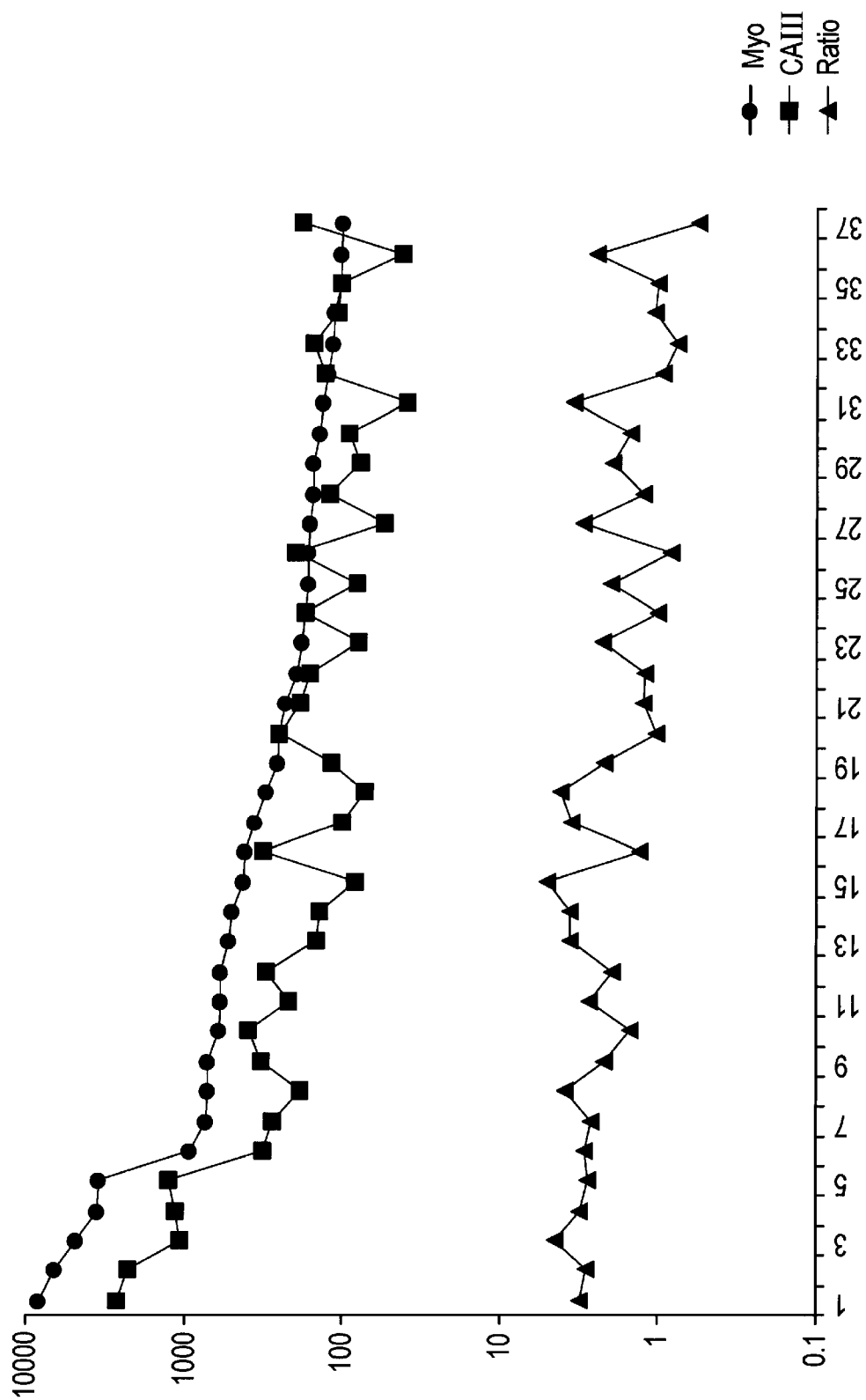
FIG. 4 depicts graphically the myoglobin, carbonic anhydrase III, and the ratio therebetween, in a series of patients with muscle disease.

To establish the cut-off value between a myoglobin-carbonic anhydrase III differential diagnostic of a heart attack versus that indicative of skeletal muscle damage, actual patient data from a series of myocardial infarct patients and a series of skeletal muscle damage patients were plotted (from highest to lowest myoglobin level) along with the ratio between the markers (FIGS. 3 and 4, respectively). The myocardial infarct patient mean ratio was 40.6, with a range of 4.6 to 170; that of the skeletal muscle patients was 2.3, with a range of 0.56 to 5.6. A ratio of 2.9 was selected as the cutoff for diagnosis of a suspected heart attack.

Figure 5:
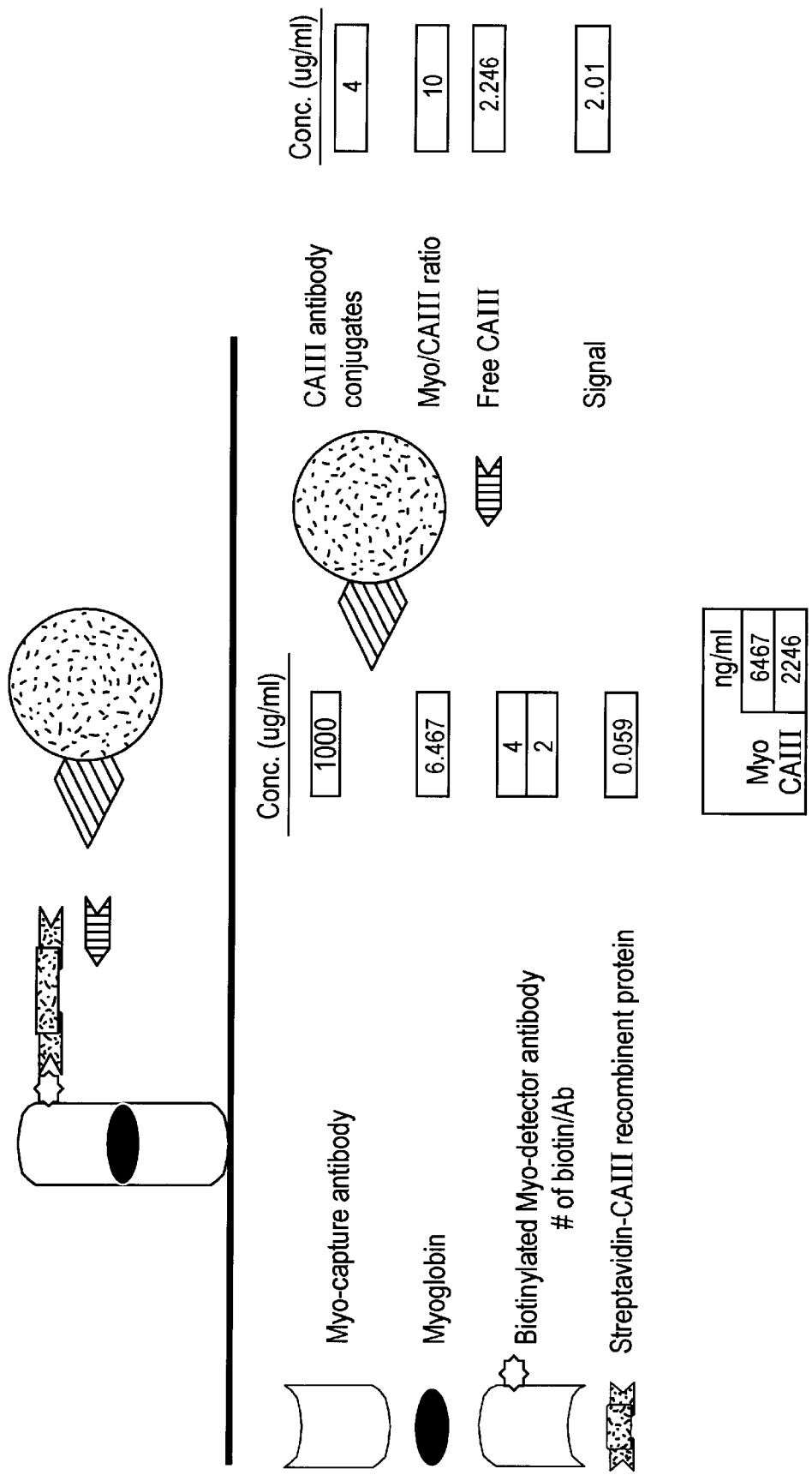
FIG. 5 shows a depiction of an assay of the invention, with levels of the components used in modeling the signal needed to achieve the desired readout.
Figure 6:
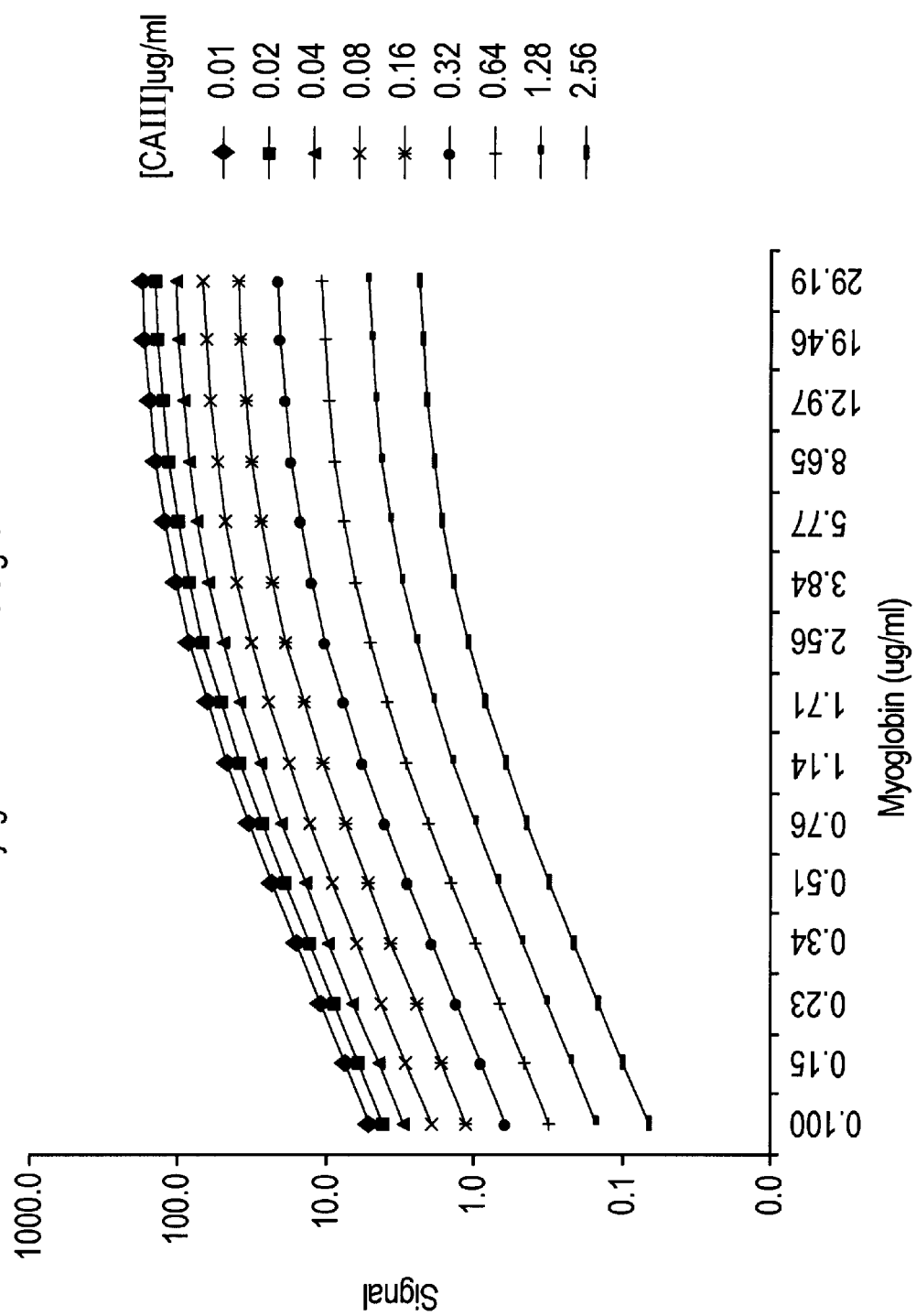
FIG. 6 shows a theoretical analysis of the signal needed for various combinations of levels of myoglobin and carbonic anhydrase.
Figure 7:
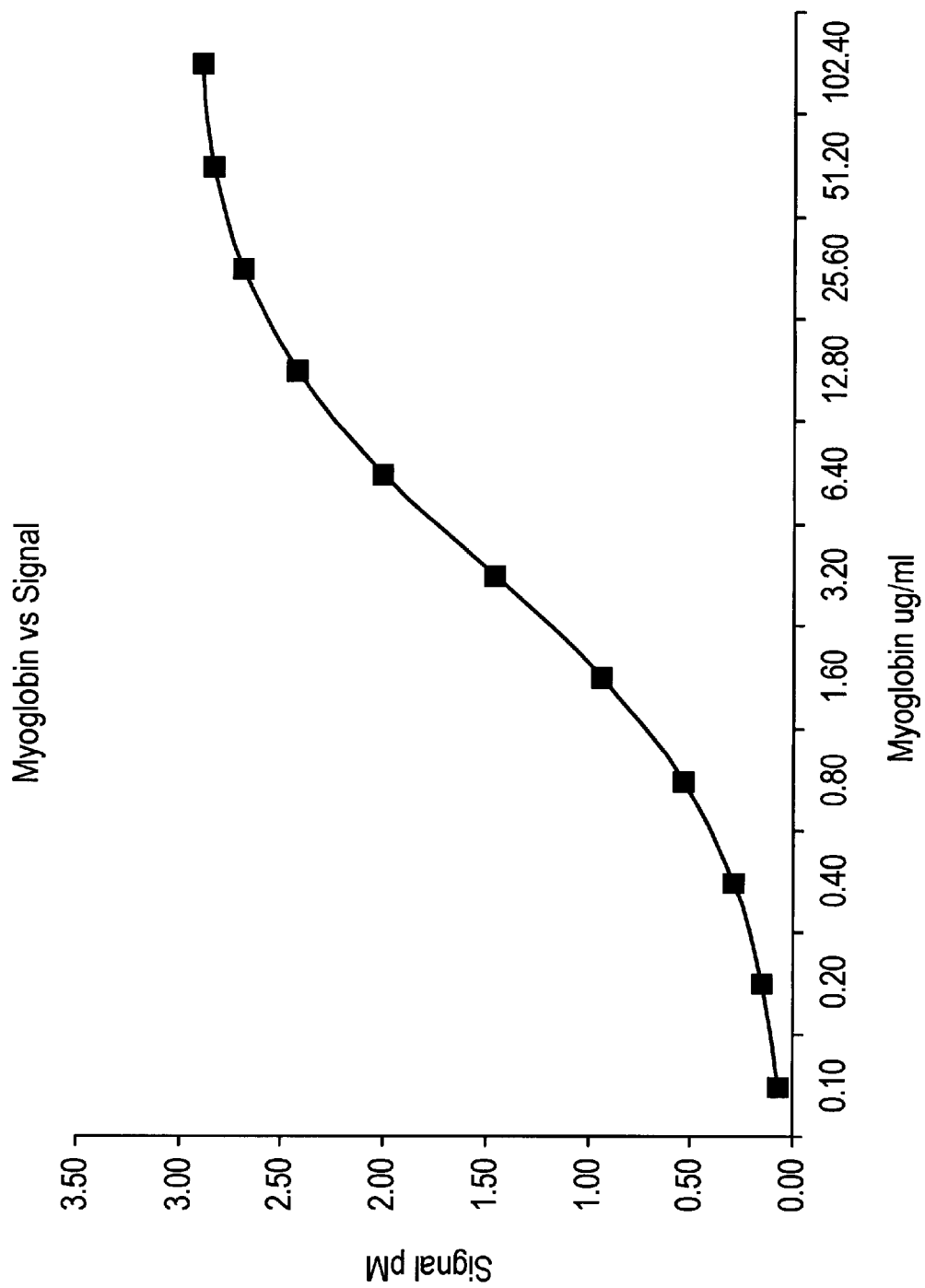
FIG. 7 shows the signal generated from a mathematical model of the present assay over a dose range of myoglobin with a myoglobin to carbonic anhydrase ratio of 2.9, and a carbonic anhydrase level of 2246 ng/ml.
Figure 8:
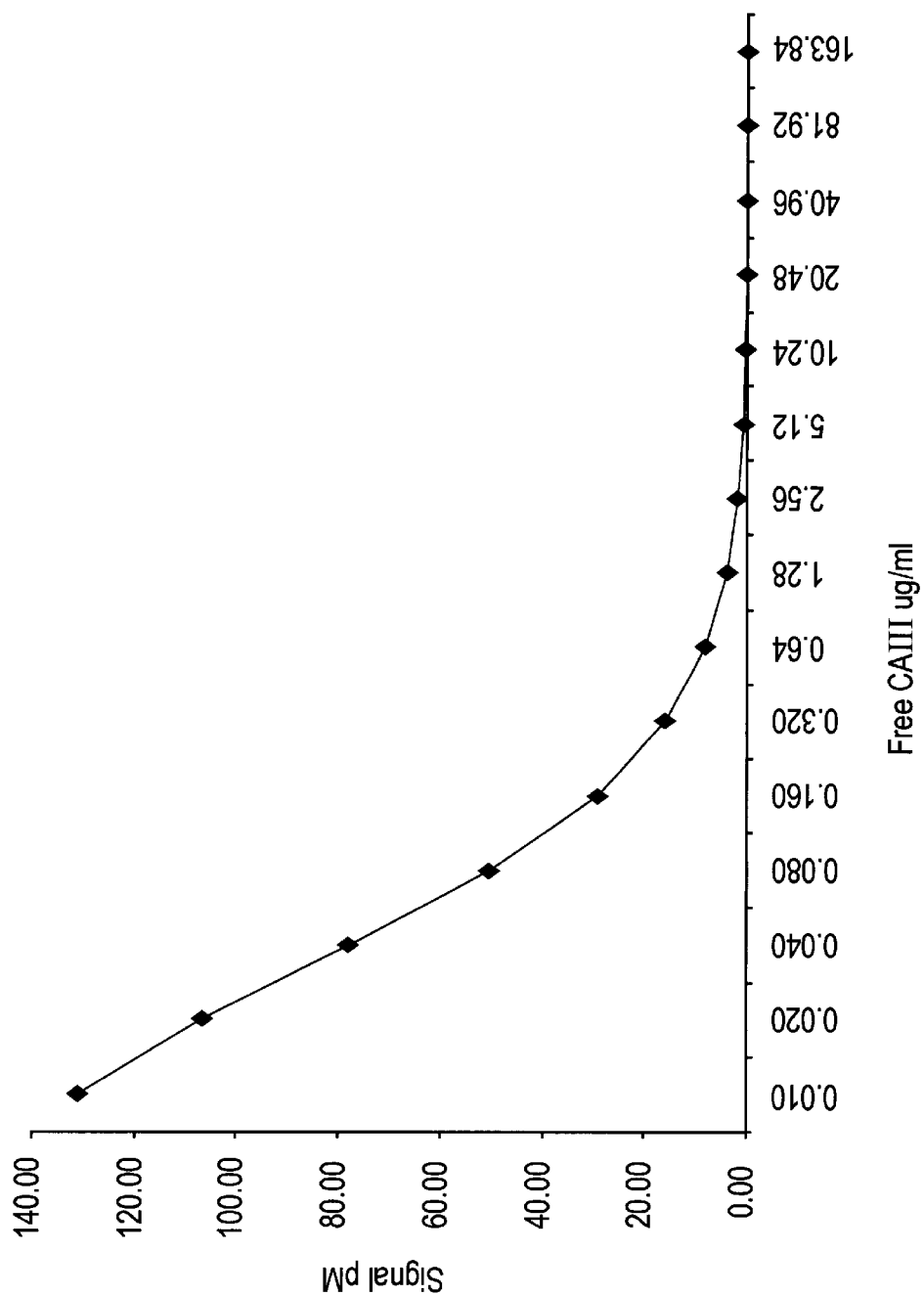
FIG. 8 shows the signal from a mathematical model of the present assay in the presence of a range of free carbonic anhydrase III, with a myoglobin:carbonic anhydrase ratio of 2.9, and 6467 ng/ml of myoglobin.

A model system with the necessary reagents was set up, according to FIG. 5. The detectable signal achieved by the assay at various levels of carbonic anhydrase III and myoglobin are shown in FIG. 6, with a horizontal line drawn at a signal level of 4.6 for heart attack patients (and 5.06 for non-heart attack patients), the detectable cut-off level. Using a myoglobin:carbonic anhydrase ratio of 2.9 and a free carbonic anhydrase level of 2246 ng/ml ($8.02 \times 10^{-8}$ M), the signal generated over a range of myoglobin levels is shown in FIG. 7. Likewise, in FIG. 8, the signal generated over a range of carbonic anhydrase values for a ratio of 2.9 and a free myoglobin level of 6467 ng/ml ($3.59 \times 10^{-7}$ M) is shown.

Figure 9:
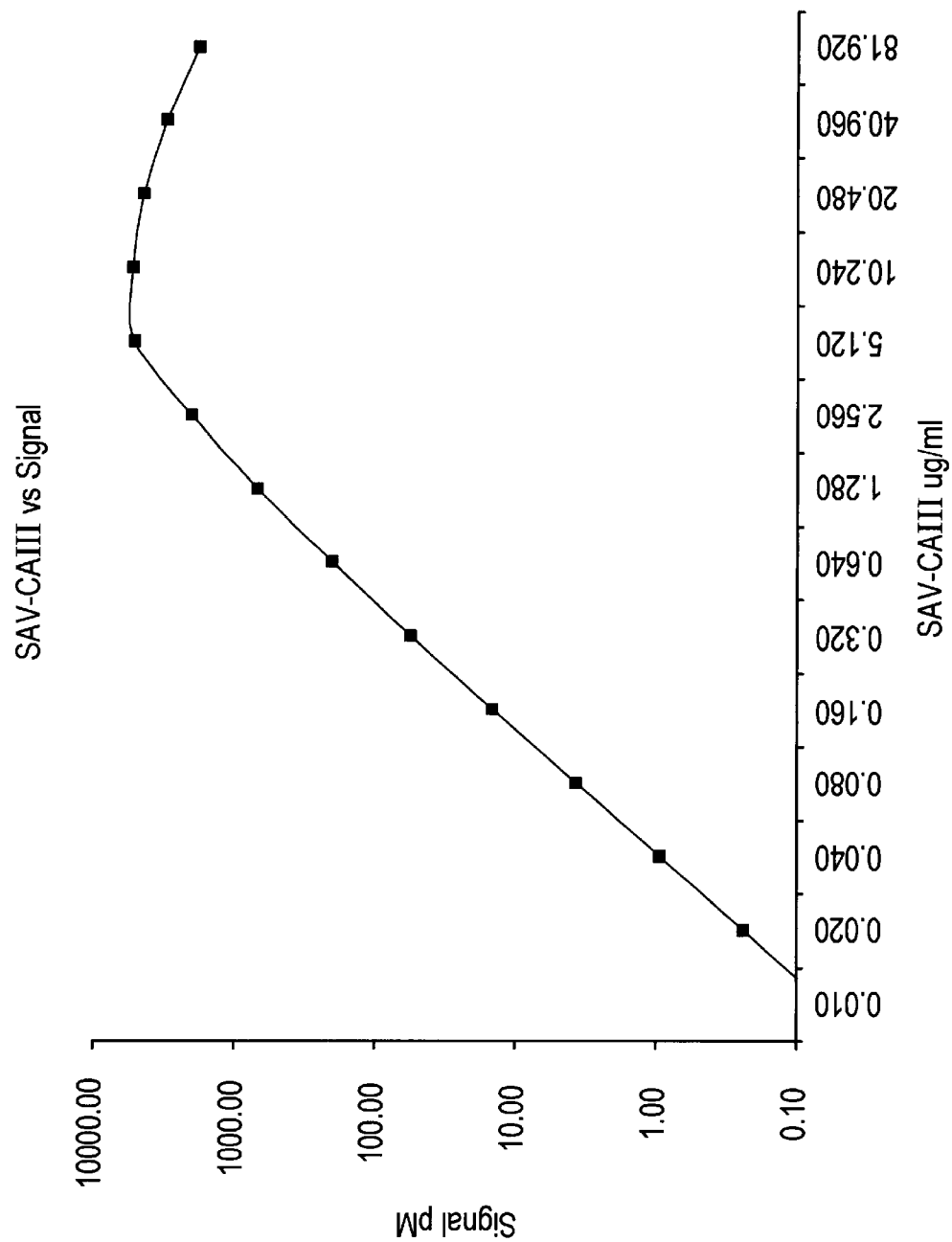
FIG. 9 shows the signal generated from a mathematical model of the present assay from a range of streptavidin-carbonic anhydrase III conjugate.
Figure 10:
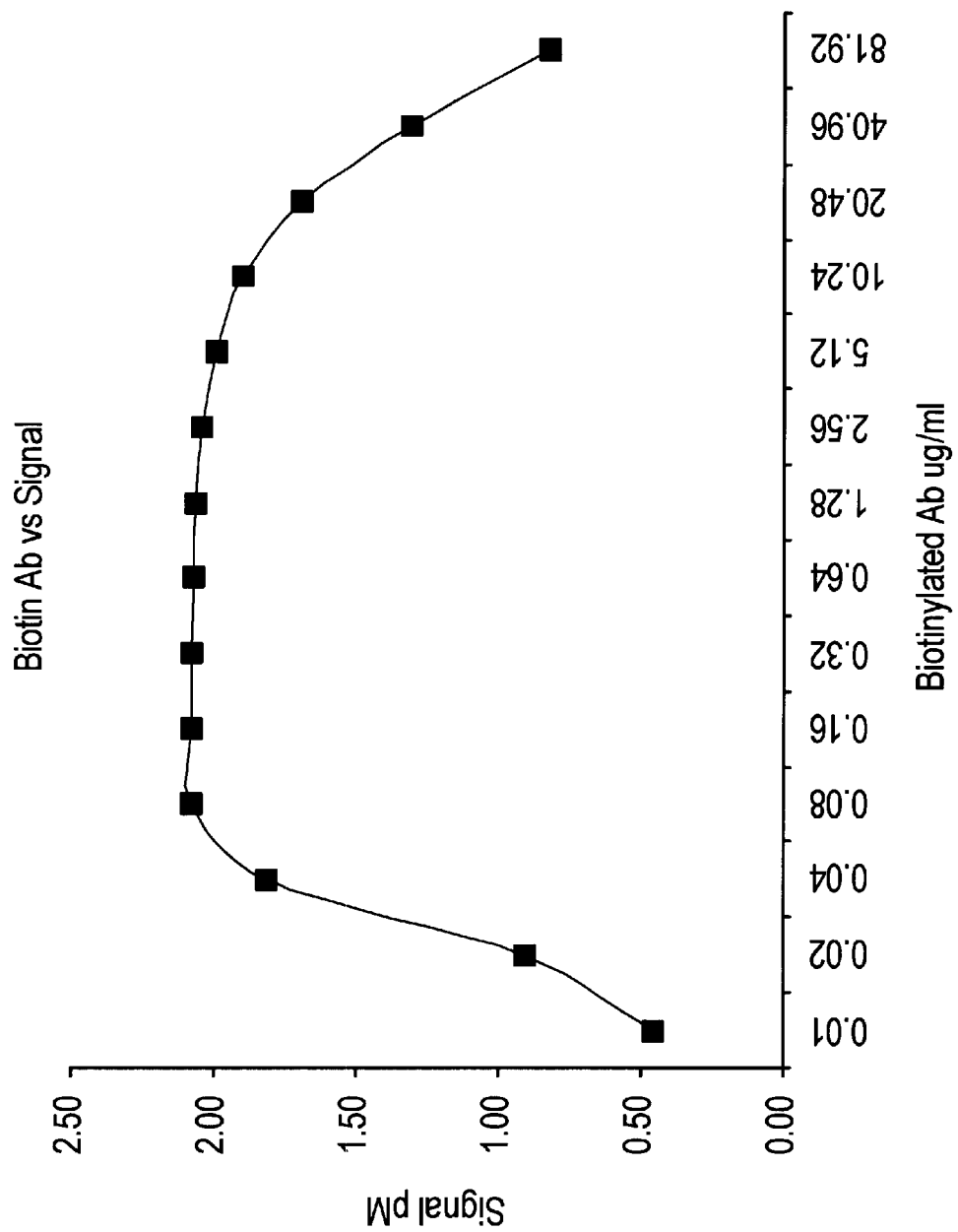
FIG. 10 shows the signal generated from a mathematical model of the present assay from a range of biotinylated antibody levels.
Figure 11:
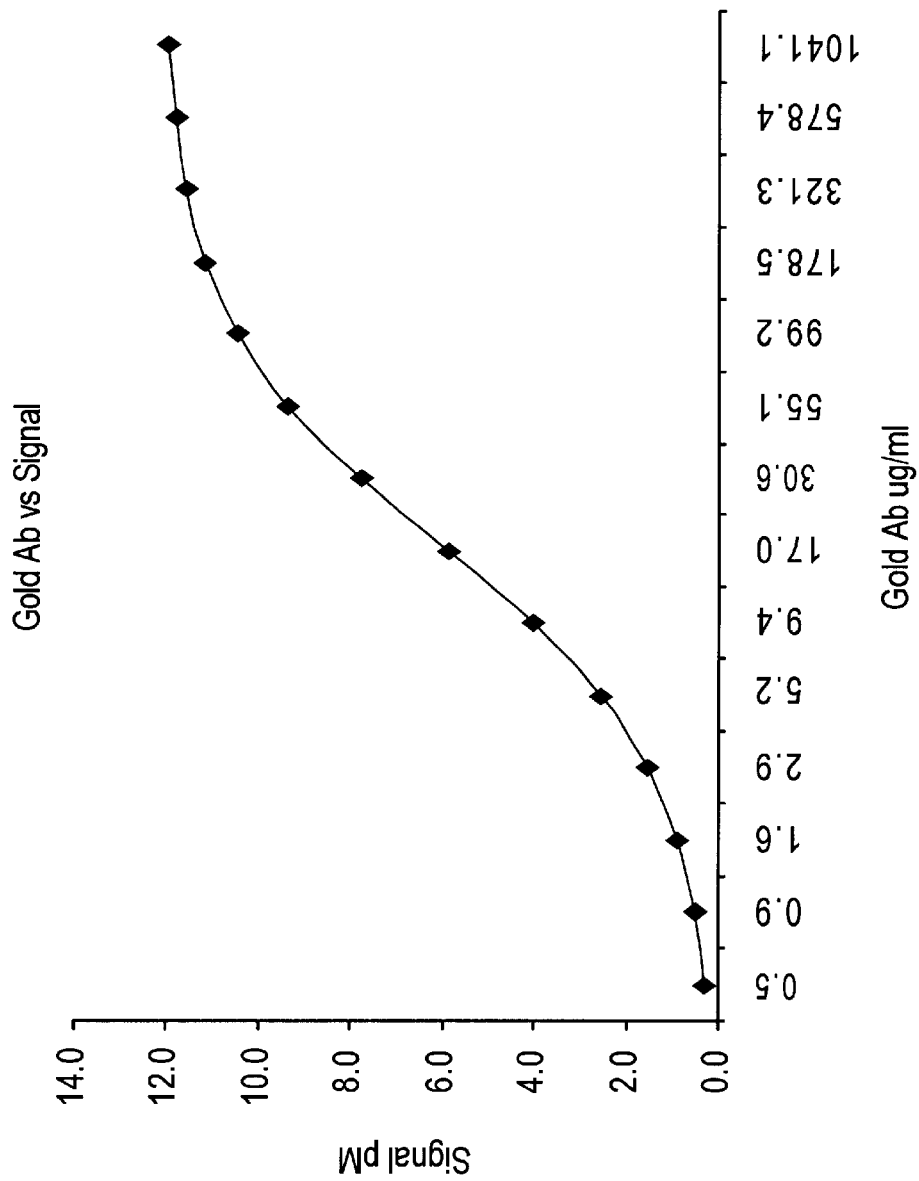
FIG. 11 shows the signal generated from a mathematical model of the present assay from a range of gold-conjugated antibody.

FIG. 9 depicts the effect of different amount of the streptavidin-carbonic anhydrase III (SAV-CAIII) conjugate, and FIG. 10 the amount of biotinylated mobile antibody. FIG. 11 shows the signal for a range of gold-labeled antibody.

EXAMPLE 4

Preparation of a Single-chain Streptavidin-carbonic Anhydrase III Polypeptide (SAV-CAIII)

In order to establish a model system, a single-chain polypeptide comprising streptavidin and carbonic anhydrase III ("SAV-CAIII") was prepared and expressed. SAV and CAIII were linked by insertion of a restriction site at the C-terminus of SAV and N-terminus of CAIII. This site resulted in an addition of two extra amino acid residues, Thr and Arg, between SAV and CAIII as indicated in SEQ ID NO:1 and FIGS. 12A–B. This polynucleotide (SEQ ID NO:2) was inserted into pet expression vector and expressed in *E. coli*.

Figure 13:
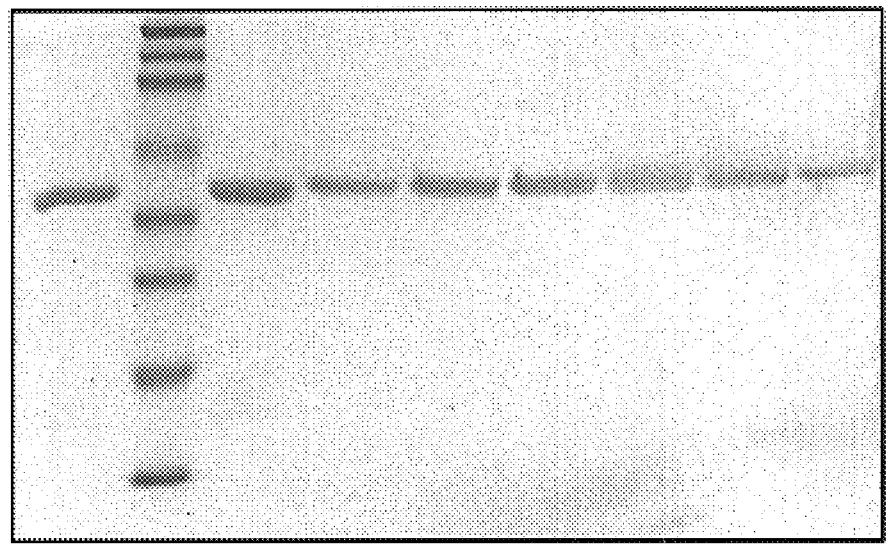
FIG. 13 shows the electrophoretic purity of the streptavidin-carbonic anhydrase III single-chain polypeptide described in FIG. 12.

The polypeptide retained biotin-binding affinity as well as recognition by anti-carbonic anhydrase III antibodies. It was electrophoretically pure (FIG. 13). A test utilizing a gold-labeled anti-carbonic anhydrase polyclonal antibody (2CA-4) at 60 micrograms/ml, the foregoing SAV-CAIII conjugate at 27.6 micrograms/ml, and a biotinylated monoclonal anti-troponin I antibody were combined. Using a BIAcore device to measure extent of complex formation, the foregoing combination generated 211 relative units. However, when wild-type streptavidin was used in place of the single-chain polypeptide, the value was 10 relative units. And in the absence of the single-chain polypeptide, the value was 11 relative units. This preliminary study establishes the capability of the biotinylated antibody to bind the streptavidin-carbonic anhydrase III single-chain polypeptide, which in turn is capable of binding the gold-labeled anti-carbonic anhydrase III antibody.

EXAMPLE 5

Assay of the Invention

In a demonstration of the operation of the assay of the invention, the following reagents were used. A rabbit anti-myoglobin capture antibody was immobilized to a surface. The mobile reagents included 1) a biotinylated anti-myoglobin antibody (2 MB-295); 2) the above-mentioned SAV-CAIII single-chain polypeptide; and 3) gold-labeled anti-myoglobin antibody (2CA-4). A strip-type test was performed with 500 ng/ml myoglobin and another with 500 ng/ml myoglobin and 500 ng/ml carbonic anhydrase III. The former gave a value of 0.155, and the latter 0.086. This illustrates the achievement of an object of the invention.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated herein by reference in their entireties.

What is claimed is:

1. An isolated conjugate comprising an analyte and streptavidin or a biotin-binding component thereof, which comprises the amino acid sequence as set forth in SEQ ID NO:1, wherein independently, said analyte in said conjugate is capable of being bound by an antibody to said analyte, and said streptavidin or biotin-binding component thereof in said conjugate is capable of binding to biotin.

2. The conjugate of claim 1 wherein said analyte is a protein or peptide.

3. The conjugate of claim 2 wherein said analyte and said streptavidin or biotin-binding component thereof reside on a single polypeptide chain.

4. The conjugate of any of claims 1 through 3 wherein said analyte is carbonic anhydrase III.

5. An isolated polynucleotide encoding the conjugate of claim 1.

6. An isolated polynucleotide encoding the conjugate of claim 4.

7. An isolated polynucleotide comprising the sequence as set forth in SEQ ID NO:2.

* * * * *

SEQUENCE LISTING

<160> NUMBER OF SEQ ID NOS: 2

<210> SEQ ID NO 1
<211> LENGTH: 421
<212> TYPE: PRT
<213> ORGANISM: homosapien

<400> SEQUENCE: 1

```
Met Asp Pro Ser Lys Asp Ser Lys Ala Gln Val Ser Ala Ala Glu Ala
 1               5                  10                  15

Gly Ile Thr Gly Thr Trp Tyr Asn Gln Leu Gly Ser Thr Phe Ile Val
            20                  25                  30

Thr Ala Gly Ala Asp Gly Ala Leu Thr Gly Thr Tyr Glu Ser Ala Val
        35                  40                  45

Gly Asn Ala Glu Ser Arg Tyr Val Leu Thr Gly Arg Tyr Asp Ser Ala
    50                  55                  60

Pro Ala Thr Asp Gly Ser Gly Thr Ala Leu Gly Trp Thr Val Ala Trp
65                  70                  75                  80

Lys Asn Asn Tyr Arg Asn Ala His Ser Ala Thr Thr Trp Ser Gly Gln
                85                  90                  95

Tyr Val Gly Gly Ala Glu Ala Arg Ile Asn Thr Gln Trp Leu Leu Thr
            100                 105                 110

Ser Gly Thr Thr Glu Ala Asn Ala Trp Lys Ser Thr Leu Val Gly His
        115                 120                 125

Asp Thr Phe Thr Lys Val Lys Pro Ser Ala Ala Ser Ile Asp Ala Ala
    130                 135                 140

Lys Lys Ala Gly Val Asn Asn Gly Asn Pro Leu Asp Ala Val Gln Gln
145                 150                 155                 160

Thr Arg Ala Lys Glu Trp Gly Tyr Ala Ser His Asn Gly Pro Asp His
                165                 170                 175

Trp His Glu Leu Phe Pro Asn Ala Lys Gly Glu Asn Gln Ser Pro Val
            180                 185                 190

Glu Leu His Thr Lys Asp Ile Arg His Asp Pro Ser Leu Gln Pro Trp
        195                 200                 205

Ser Val Ser Tyr Asp Gly Gly Ser Ala Lys Thr Ile Leu Asn Asn Gly
    210                 215                 220

Lys Thr Cys Arg Val Val Phe Asp Asp Thr Tyr Asp Arg Ser Met Leu
225                 230                 235                 240

Arg Gly Gly Pro Leu Pro Gly Pro Tyr Arg Leu Arg Gln Phe His Leu
                245                 250                 255

His Trp Gly Ser Ser Asp Asp His Gly Ser Glu His Thr Val Asp Gly
            260                 265                 270

Val Lys Tyr Ala Ala Glu Leu His Leu Val His Trp Asn Pro Lys Tyr
        275                 280                 285

Asn Thr Phe Lys Glu Ala Leu Lys Gln Arg Asp Gly Ile Ala Val Ile
    290                 295                 300

Gly Ile Phe Leu Lys Ile Gly His Glu Asn Gly Glu Phe Gln Ile Phe
305                 310                 315                 320

Leu Asp Ala Leu Asp Lys Ile Lys Thr Lys Gly Lys Glu Ala Pro Phe
                325                 330                 335

Thr Lys Phe Asp Pro Ser Cys Leu Phe Pro Ala Cys Arg Asp Tyr Trp
            340                 345                 350

Thr Tyr Gln Gly Ser Phe Thr Thr Pro Pro Cys Glu Glu Cys Ile Val
```

-continued

```
Trp Leu Leu Lys Glu Pro Met Thr Val Ser Ser Asp Gln Met Ala
    370                 375                 380

Lys Leu Arg Ser Leu Leu Ser Ser Ala Glu Asn Glu Pro Pro Val Pro
385                 390                 395                 400

Leu Val Ser Asn Trp Arg Pro Pro Gln Pro Ile Asn Asn Arg Val Val
                405                 410                 415

Arg Ala Ser Phe Lys
            420

<210> SEQ ID NO 2
<211> LENGTH: 1266
<212> TYPE: DNA
<213> ORGANISM: homosapien

<400> SEQUENCE: 2
atggacccct ccaaggactc gaaggcccag gtctcggccg ccgaggccgg catcaccggc        60
acctggtaca accagctcgg ctcgaccttc atcgtgaccg cgggcgccga cggcgccctg       120
accggaacct acgagtcggc cgtcggcaac gccgagagcc gctacgtcct gaccggtcgt       180
tacgacagcg ccccggccac cgacggcagc ggcaccgccc tcggttggac ggtggcctgg       240
aagaataact accgcaacgc ccactccgcg accacgtgga cggccagta cgtcggcggc       300 gccgaggcga ggatcaacac ccagtggctg ctgacctccg caccaccga ggccaacgcc       360 tggaagtcca cgctggtcgg ccacgacacc ttcaccaagg tgaagccgtc cgccgcctcc       420
atcgacgcgg cgaagaaggc cggcgtcaac aacggcaacc cgctcgacgc cgttcagcag       480
actagggcca aggagtgggg ctacgccagt cacaacggtc ctgaccactg gcatgaactt       540
ttcccaaatg ccaaggggga aaaccagtcg cccgttgagc tgcatactaa agacatcagg       600
catgacccct ctctgcagcc atggtctgtg tcttatgatg gtggctctgc caagaccatc       660
ctgaataatg ggaagaccctg ccgagttgta tttgatgata cttatgatag gtcaatgctg       720 agaggggtc ctctccctgg accctaccga cttcgccagt ttcatcttca ctggggctct       780
tcggatgatc atggctctga gcacaccgtg gatggagtca agtatgcagc ggagcttcat       840
ttggttcact ggaacccgaa gtataacact tttaagaag ccctgaagca gcgcgatggg       900
atcgctgtga ttggcatttt tctgaagata ggacatgaga atggcgagtt ccagattttc       960
cttgatgcat tggacaagat taagacaaag ggcaaggagg cgcccttcac aaagtttgac      1020
ccatcctgcc tgttcccggc atgccgggac tactggacct accagggctc attcaccacg      1080
ccgccctgcg aggaatgcat tgtgtggctg ctgctgaagg agcccatgac cgtgagctct      1140
gaccagatgg ccaagctgcg gagcctcctc tccagtgctg agaacgagcc cccagtgcct      1200
cttgtgagca actggcgacc tccacagcct atcaataaca gggtggtgag agcttccttc      1260
aaatga                                                                 1266
```